United States Patent
Yurube et al.

(10) Patent No.: US 11,951,231 B2
(45) Date of Patent: Apr. 9, 2024

(54) THERAPEUTIC AGENT FOR INTERVERTEBRAL DISC DEGENERATION AND MATERIAL FOR CULTURING INTER VERTEBRAL DISC CELLS

(71) Applicants: NATIONAL UNIVERSITY CORPORATION KOBE UNIVERSITY, Hyogo (JP); KINKI UNIVERSITY, Osaka (JP); FOUNDATION FOR BIOMEDICAL RESEARCH AND INNOVATION AT KOBE, Hyogo (JP)

(72) Inventors: Takashi Yurube, Hyogo (JP); Yoshiki Takeoka, Hyogo (JP); Koichi Morimoto, Wakayama (JP); Saori Kunii, Wakayama (JP); Kaoru Omae, Hyogo (JP)

(73) Assignee: KINKI UNIVERSITY, Osaka (JP)

( * ) Notice: Subject to any disclaimer, the term of this patent is extended or adjusted under 35 U.S.C. 154(b) by 547 days.

(21) Appl. No.: 16/966,226

(22) PCT Filed: Jan. 31, 2019

(86) PCT No.: PCT/JP2019/003494
§ 371 (c)(1),
(2) Date: Jul. 30, 2020

(87) PCT Pub. No.: WO2019/151444
PCT Pub. Date: Aug. 8, 2019

(65) Prior Publication Data
US 2021/0046214 A1 Feb. 18, 2021

(30) Foreign Application Priority Data
Jan. 31, 2018 (JP) ................. 2018-015541

(51) Int. Cl.
| | |
|---|---|
| *A61L 27/24* | (2006.01) |
| *A61K 38/39* | (2006.01) |
| *A61L 27/50* | (2006.01) |
| *A61L 27/52* | (2006.01) |
| *A61L 27/54* | (2006.01) |
| *A61P 19/08* | (2006.01) |
| *A61P 43/00* | (2006.01) |
| *C07K 1/12* | (2006.01) |
| *C07K 14/78* | (2006.01) |
| *C12M 1/00* | (2006.01) |
| *C12N 5/00* | (2006.01) |
| *C12N 5/077* | (2010.01) |

(52) U.S. Cl.
CPC ............ *A61L 27/24* (2013.01); *A61L 27/50* (2013.01); *A61L 27/52* (2013.01); *C07K 14/78* (2013.01); *C12N 5/0655* (2013.01)

(58) Field of Classification Search
None
See application file for complete search history.

(56) References Cited

U.S. PATENT DOCUMENTS

| | | | |
|---|---|---|---|
| 6,340,369 | B1 | 1/2002 | Ferree |
| 10,155,804 | B2 * | 12/2018 | Morimoto ............. A61K 38/17 |
| 2005/0002909 | A1 | 1/2005 | Moehlenbruck et al. |
| 2010/0021439 | A1 | 1/2010 | Moehlenbruck et al. |

FOREIGN PATENT DOCUMENTS

| | | |
|---|---|---|
| CN | 1875988 | 12/2006 |
| CN | 101198297 | 6/2008 |
| CN | 105030828 | 11/2015 |
| CN | 107496060 | 12/2017 |
| JP | 2003-530364 | 10/2003 |
| JP | 2006-508771 | 3/2006 |
| WO | 2004/026189 | 4/2004 |
| WO | 2007/131424 | 11/2007 |
| WO | 2010/129692 | 11/2010 |
| WO | 2015/167003 | 11/2015 |
| WO | 2015/167004 | 11/2015 |
| WO | 2017/163603 | 9/2017 |

OTHER PUBLICATIONS

Moghadam et al. (Differentiation of Rat bone marrow Mesenchymal stem cells into Adipocytes and Cardiomyocytes after treatment with platelet lysate, International Journal of Hematology-Oncology and Stem Cell Research, vol. 10, No. 1, Jan. 1, 2016).*
Cho et al. (Chitosan Gel as an In Situ—Forming Scaffold for Rat Bone Marrow Mesenchymal Stem Cells In Vivo, Tissue Engineering: Part A, vol. 14, No. 6, 2008, pp. 1099-1108).*
Takeoka et al., "Reduced Nucleotomy-induced Intervertebral Disc Disruption Through Spontaneous Spheroid Formation by the Low Adhesive Scaffold Collagen (LASCol)", *Biomaterials*, vol. 235, pp. 1-15 (2020).
Kunii et al., "Low Adhesive Scaffold Collagen Promotes the Osteogenic Differentiation of Rat Marrow Mesenchymal Cells", *Bone Abstracts*, vol. 5, p. 154 (2016).
Lian et al., "Collagen Type II is Downregulated in the Degenerative Nucleus Pulposus and Contributes to the Degeneration and Apoptosis of Human Nucleus Pulposus Cells", *Molecular Medicine Reports*, vol. 16, pp. 4730-4736 (2017).
Ren et al., "Advances in intervertebral disc tissue engineering research", *Chinese Journal of Spine and Spinal Cord*, vol. 16, No. 4, pp. 297-300 (2006), including English language Abstract.

(Continued)

*Primary Examiner* — Suzanne M Noakes
*Assistant Examiner* — Jae W Lee
(74) *Attorney, Agent, or Firm* — Greenblum & Bernstein, P.L.C.

(57) ABSTRACT

A therapeutic agent for intervertebral disc degeneration that contains LASCol obtained by enzymatically cleaving a terminus of collagen.

6 Claims, 28 Drawing Sheets

Specification includes a Sequence Listing.

(56) References Cited

OTHER PUBLICATIONS

Office Action issued in CN Patent Application No. 201980011055.3, dated Oct. 11, 2021.
Lee et al., "Tissue Engineering of the Intervertebral Disc With Cultured Nucleus Pulposus Cells Using Atelocollagen Scaffold and Growth Factors", *Spine*, vol. 37, No. 6, pp. 452-458 (2012).
Morimoto et al., "Preparation and Structural Analysis of Actinidain-processed Atelocollagen of Yellowfin Tuna (*Thunnus albacares*)", *Bioscience, Biotechnology, and Biochemistry*, vol. 68, No. 4, pp. 861-867 (2004).
Masuda et al., "Osteogenic Protein-1 Injection Into a Degenerated Disc Induces the Restoration of Disc Height and Structural Changes in the Rabbit Anular Puncture Model", *Spine*, vol. 31, No. 7, pp. 742-754 (2006).
Takeoka et al., "Possibility of Intervertebral Disc Regeneration by the Low Adhesive Scaffold Collagen (LASCol)", *Journal of Spine Research*, vol. 9, No. 3, pp. 233 (2018), along with English language translation.
Tang et al., "A New Non-enzymatic Method for Isolating Human Intervertebral Disc Cells Preserves the Phenoype of Nucleus Pulposus Cells", *Cytotechnology*, vol. 66, pp. 979-986 (2014).
International Search Report issued in PCT/JP2019/003494, dated Apr. 2, 2019, along with an English language translation.

\* cited by examiner

Fig. 3
SPHEROID OF RAT ANNULUS FIBROSUS CELLS FORMED ON GEL
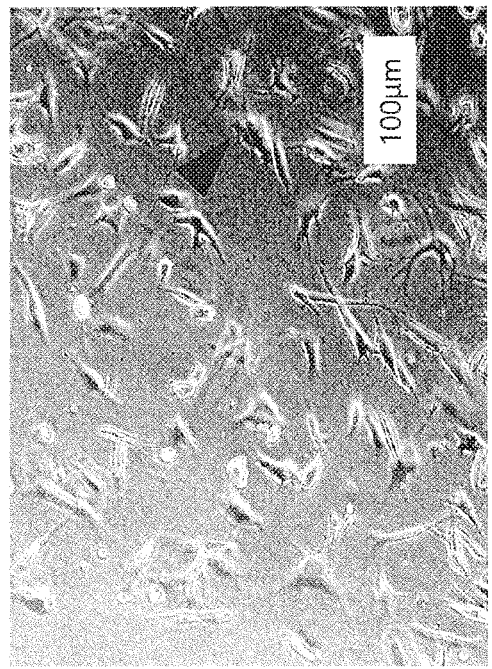
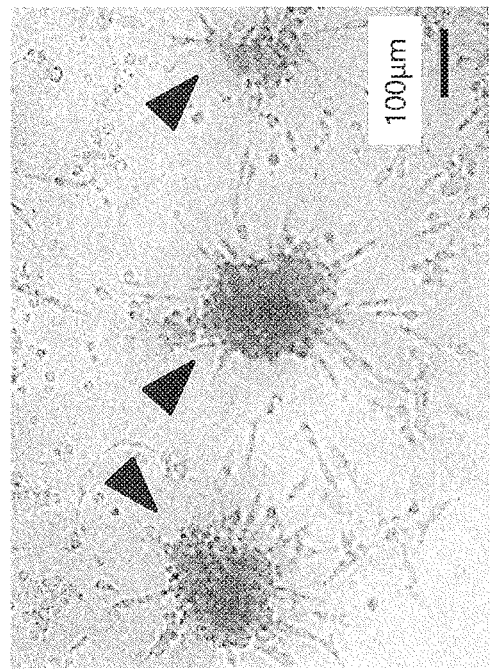
(a) LAScol GEL
(b) LAScol GEL Fig. 14
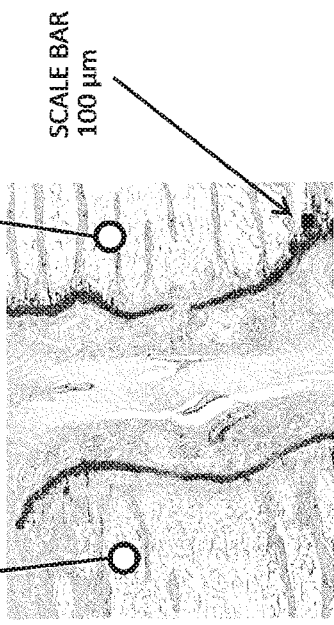
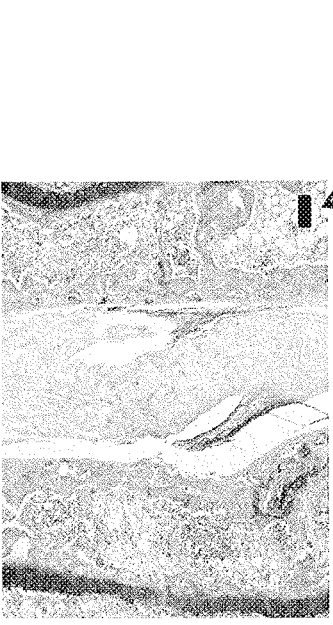

THERAPEUTIC AGENT FOR INTERVERTEBRAL DISC DEGENERATION AND MATERIAL FOR CULTURING INTER VERTEBRAL DISC CELLS

FIELD

The present invention relates to a therapeutic agent for use in treatment of intervertebral disc degeneration in a spine and a method thereof. The present invention also includes a material for culturing intervertebral disc cells.

BACKGROUND

A human's spine is a column of vertebrae that are connected longitudinally, in which a vertebra is composed of a vertebral body, a vertebral arch, a spinous process, and the like. An intervertebral disc is located between the vertebrae as a cushioning material and enables movement of an entire spine such as bending, stretching, or rotating. Such an intervertebral disc is composed of a laminar structure called annulus fibrosus, which is made of annular fibers, and jelly-like nucleus pulposus, which is surrounded by the annulus fibrosus and includes a chondrocyte that produces collagen and a proteoglycan.

A condition in which a normal positional relationship between the nucleus pulposus and the annulus fibrosus has been disrupted in the intervertebral disc for some reason is referred to as intervertebral disc herniation. Loss of normal cushioning property causes local pain such as backache. Furthermore, when herniated nucleus pulposus compresses a neighboring nerve tissue, radiating pain occurs in the innervated area. Examples of common symptoms thereby include sciatica.

For example, surgical therapy that surgically removes the herniated nucleus pulposus is used for treating intervertebral disc herniation. However, it is reported that, after surgical therapy, loss of the nucleus pulposus leads to narrowing of an intervertebral space, and age-related change, that is, degeneration of a vertebral column progresses over time.

When a distance between vertebrae is shortened, shock absorbency is reduced, thereby inducing local pain. Furthermore, reduced stability of the vertebral column leads to slippage of the vertebrae, resulting in spinal canal stenosis, which causes neuropathy such as sciatica. Therefore, there has been a long-standing demand for a filler that can maintain the intervertebral disc. However, when the filler is simply filled into the intervertebral disc, the filler protrudes and a disorder similar to hernia reoccurs. Accordingly, there has been a strong demand for a filler that can be expected to maintain a certain distance between vertebrae over a long period of time by settling in a place where the nucleus pulposus originally existed and regenerating tissue.

The extracellular matrix of the nucleus pulposus is composed mainly of aggrecan and type II collagen, and cells constituting the nucleus pulposus originate from a notochord. The extracellular matrix of the annulus fibrosus is composed mainly of aggrecan and type I collagen, and cells constituting the annulus fibrosus originate from mesenchyme. Therefore, collagen has been conventionally used as a substitute material for damaged nucleus pulposus (Patent Literature 1).

On the other hand, Patent Literature 2 discloses a matrix for treating a patient with a degenerative intervertebral disc disease, wherein the matrix includes an injectable fluid that contains digestion-resistant and remodelable collagen, the collagen being cross-linked by photooxidation catalysis and irradiation with visible light; and a plurality of living cells that have an unique ability to synthesize a proteoglycan in vivo, the living cells being dispersed in the above-mentioned injectable fluid so as to form an injectable cell matrix for treating the degenerative intervertebral disc disease. The invention of Patent Literature 2 is not merely for maintaining a certain distance between vertebrae but for promoting regeneration of a nucleus pulposus cell.

Collagen is a material that has bioaffinity and is readily available. It is known that there are many types of collagen. Collagen has a triple helical structure composed of α chains. Patent Literature 3 describes low adhesive collagen (Low Adhesive Scaffold Collagen, hereinafter referred to as "LASCol") that was produced by cleaving a terminus of these α chains by using a specified enzyme. LASCol is also known as a scaffold material for culturing cells (Patent Literature 4).

When a scaffold using LASCol is utilized instead of a scaffold using conventional collagen, cells to be cultured form an aggregate (spheroid), and thus, the cells to be cultured can be cultured in a three-dimensional form, which is more similar to in vivo state. Such LASCol is also effective in promoting induction of differentiation of stem cells (Patent Literature 4).

CITATION LIST

Patent Literature

Patent Literature 1: Japanese Translation of PCT Patent Application Publication No. 2006-508771
Patent Literature 2: Japanese Translation of PCT Patent Application Publication No. 2003-530364
Patent Literature 3: International Publication No. 2015/167003
Patent Literature 4: International Publication No. 2015/167004

Non-Patent Literature

Non-Patent Literature 1: K. Morimoto et al., Bioscience, Biotechnology, and Biochemistry, Vol. 68, pp. 861-867, 2004
Non-Patent Literature 2: Masuda, K., Imai, Y., Okuma, M., et al. (2006):Osteogenic protein-1 infection into a degenerated disc induces the restoration of disc height and structural changes in the rabbit annular puncture model. Spine, 31, 742-754.

SUMMARY

Technical Problem

In Patent Literature 2, the matrix to be injected as a substitute for the nucleus pulposus was intended to be obtained from a donor vertebrate and an example thereof is nucleus pulposus tissue excised aseptically from the intervertebral disc of the vertebral column of a pig. Additionally, a living cell that produces the proteoglycan has been incorporated into this matrix. It is impossible to deny that the nucleus pulposus tissue from the donor has the risk of contamination with a virus or any other substance from the donor. Furthermore, there are many unknown things such as how introduction of a heterologous living cell affects a human who received implantation.

On the other hand, in Patent Literature 1, collagen, which is a material that has bioaffinity and has been previously used in a human body, was used, but collagen has no effect of regenerating the nucleus pulposus cell. Accordingly, there has been demand for a filler that is safer and capable of regenerating the nucleus pulposus cell, the filler being injected as a substitute for nucleus pulposus.

Solution to Problem

The present invention has been devised to solve the above-mentioned problem and provides a composition (a therapeutic agent for intervertebral disc degeneration) that is injected into an annulus fibrosus as a substitute for a nucleus pulposus for treating intervertebral disc degeneration. In this context, intervertebral disc degeneration includes hernia. More specifically, the present invention provides a therapeutic agent containing LASCol that is used for treating intervertebral disc degeneration. The present invention may be described as a method for treating intervertebral disc degeneration by using LASCol.

The present invention also provides a LASCol-containing material for culturing intervertebral disc cells. In this context, the material for culturing intervertebral disc cells is a culture material that enables culturing a nucleus pulposus cell and/or an annulus fibrosus cell. Furthermore, the present invention provides a method for producing the therapeutic agent and the culture material, and a method for treating a non-human animal by using the therapeutic agent for intervertebral disc degeneration, as well as a nucleus pulposus cell and an annulus fibrosus cell regenerated by the therapeutic agent.

Advantageous Effects of Invention

The therapeutic agent for intervertebral disc degeneration according to the present invention contains LASCol and can maintain a certain distance between vertebrae, whose nucleus pulposus has escaped, over a long period of time. LASCol itself is made of collagen naturally present in the intervertebral disc and has a high affinity with the intervertebral disc, which contributes to a high level of safety. Furthermore, LASCol can allow a cell that produces a proteoglycan, a component of a nucleus pulposus, to migrate from surrounding cells and infiltrate, and thus can produce the effect of regenerating the nucleus pulposus without injecting a nucleus pulposus cell or a living cell from the outside.

BRIEF DESCRIPTION OF DRAWINGS

FIG. 3 includes photographs showing a spheroid formed by aggregation of cultured rat annulus fibrosus cells.

FIG. 14 includes photographs showing a tissue specimen of a nucleus pulposus region of a rat caudal vertebra that was stained with safranin O one week after operation.

DESCRIPTION OF EMBODIMENTS

Figure 1:
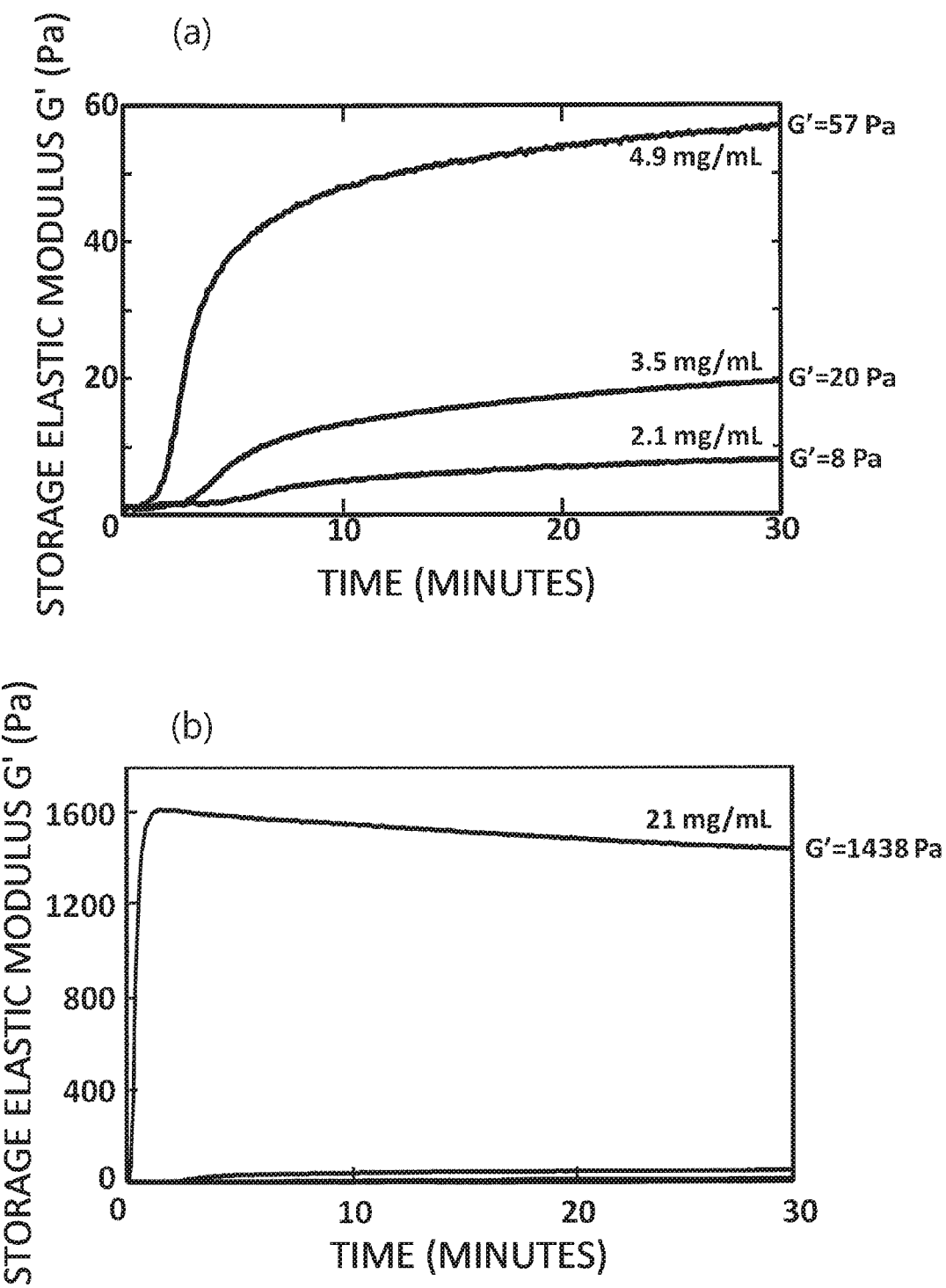
FIG. 1 includes graphs showing the relationship between a LASCol concentration and a storage elastic modulus.

Hereinafter, a therapeutic agent for intervertebral disc is degeneration and a material for culturing intervertebral disc cells according to the present invention will be described with reference to the drawings and Examples. The following description is merely illustrative of an embodiment and an example of the present invention and the present invention is not limited to the following description. The following description may be modified without departing from the spirit of the invention.

LASCol that is used as the therapeutic agent for intervertebral disc degeneration and the material for culturing intervertebral disc cells according to the present invention contains a degradation product of collagen or atelocollagen. Adhesiveness of collagen to cells has been weakened in the degradation product, and thus, the degradation product has the property of becoming low adhesive. Furthermore, the therapeutic agent for intervertebral disc degeneration according to the present invention may also contain a substance such as hydrogel, gelatin gel, chitosan gel, hyaluronic acid-collagen hydrogel, a hyaluronic acid polymer, a hyaluronic acid-PEG polymer, collagen-hyaluronic acid-PEG hydrogel, or ultra-purified alginate gel (UPAL), and/or a solvent having affinity with human body (these are collectively referred to as "auxiliary substance"). Needless to say, LASCol may be used alone. Furthermore, a buffer solution, a pH adjusting solution, a salt, or a cell growth factor may be added.

LASCol can be obtained by degrading collagen or atelocollagen enzymatically. The peptide sequence of LASCol varies depending on a degradation condition. In other words, a different type of LASCol can be obtained by using a different degradation condition.

The characteristic of LASCol that can be used in the present invention is that LASCol consists of a combination of α chains in which a chemical bond between $Y_1$ and $Y_2$ is cleaved in an amino-terminal amino acid sequence including a triple helical domain of collagen or atelocollagen, the sequence being shown below (A: SEG ID NO: 1).

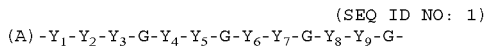

(where G represents glycine, and $Y_1$ to $Y_9$ each represent an optional amino acid)

The triple helical domain of collagen is known to have a succession of -G-X-Y- sequences (where G represents glycine, and X and Y each represent an optional amino acid). In the above-mentioned sequence, "G" in "-$Y_3$-G-$Y_4$-$Y_5$-" represents glycine on the N-terminal side of the triple helical domain. As can be seen from the above-mentioned sequence, the cleavage of the chemical bond between $Y_1$ and $Y_2$ is cleavage that was carried out outside of the triple helical domain. As described below, a different degradation condition leads to cleavage inside of the triple helical domain. One of the LASCols used in the present invention is LASCol in which cleavage has occurred outside of the triple helical domain. Hereinafter, this LASCol is referred to as LASCol-A.

It is known that the following LASCol is obtained under a certain degradation condition. Such. LASCol consists of a combination of α chains in which a chemical bond between $X_1$ and $X_2$, a chemical bond between $X_2$ and G, a chemical bond between G and $X_3$, a chemical bond between $X_4$ and G, or a chemical bond between $X_6$ and G is cleaved in an amino-terminal amino acid sequence including a triple helical domain of collagen or atelocollagen, the sequence being shown below (B: SEQ ID NO: 2).

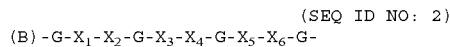

(where G represents glycine, and $X_1$ to $X_6$ each represent an optional amino acid)

This LASCol is referred to as LASCol-B. In LASCol-B, cleavage has occurred inside of the triple helical domain. In SEQ ID NO: 2, G in "-G-$X_1$-$X_2$-G-" is glycine on the N-terminal side of the triple helical domain. Needless to say, there may be other LASCols that contain other peptides. Among currently known LASCols, LASCol-A is most favorable as the therapeutic agent for intervertebral disc degeneration. However, other LASCols are not excluded.

The LASCol used as the therapeutic agent for intervertebral disc degeneration according to the present invention can be stored as a solution under an acidic condition. The LASCol turns into a gel state when pH and a concentration thereof are adjusted and a temperature thereof is raised to body temperature. Gelling suppresses diffusion of LASCol in an annulus fibrosus, and LASCol exerts the effect of maintaining a distance between vertebrae (referred to as "intervertebral space-maintaining ability") by mediating cell induction and/or production of an extracellular matrix and achieving tissue regeneration.

The elastic modulus of gelled LASCol is proportional to the concentration and pH of LASCol in the solution, and temperature. In Examples described below, an embodiment is illustrated in which the pH and concentration of LASCol are adjusted to prepare liquid LASCol, and the liquid LASCol is sucked into a syringe and administered by injection into the annulus fibrosus, thereby allowing the LASCol to turn into gel or in the annulus fibrosus. Alternatively, the LASCol used as the therapeutic agent for intervertebral disc degeneration according to the present invention may be shaped into a film form or a sponge form and be implanted in an affected part. In this context, the film form or the sponge form refers to LASCol that was dried to form a specified shape (also referred to as a shaped form).

Furthermore, LASCol may be used with the auxiliary substance in the therapeutic agent for intervertebral disc degeneration. In such a therapeutic agent for intervertebral disc degeneration, the auxiliary substance provides mechanical strength to develop the intervertebral space-maintaining ability, and LASCol plays a role in allowing a cell that produces a proteoglycan, a component of a nucleus pulposus, to migrate from surrounding cells and infiltrate, thereby regenerating a nucleus pulposus cell.

As described below, it can be stated that the LASCol used in the present invention turns into gel when a concentration thereof is 3.5 mg/ml (20 Pa in terms of "practical elastic modulus" described below) or more. Therefore, LASCol at this concentration or a higher concentration can be mixed with the auxiliary substance to obtain the therapeutic agent for intervertebral disc degeneration that regenerates the nucleus pulposus cell and the material for culturing intervertebral disc cells.

Furthermore, LASCol at a concentration of 7 mg/ml or higher has, by itself, the intervertebral space-maintaining ability, and LASCol at a concentration of 21 mg/ml or higher has, by itself, a greater intervertebral space-maintaining ability than atelocollagen.

Therefore, LASCol that can be used in the present invention can be used at a concentration of 3.5 mg/ml or higher, preferably 7 mg/ml or higher, and more preferably 21 mg/ml or higher. Although the upper limit of the concentration of LASCol in a gel form is at least 42 mg/ml or higher, LASCol can still be utilized as the therapeutic agent for intervertebral disc degeneration at a concentration equal to or higher than the upper limit.

Findings about a method for producing LASCol are almost the same for both LASCol-B and LASCol-A. Thus, findings common to both are described simply as findings about LASCol. In the following description, "degradation product" means LASCol.

<Material for LASCol>

Collagen or atelocollagen as a material for LASCol is not limited to any particular one and may be any well-known collagen or atelocollagen.

Examples of the collagen include collagens of mammals (for example, a cow, a pig, a rabbit, a human, a rat, or a mouse), birds (for example, a chicken), fishes (for example, a shark, a carp, an eel, a tuna [for example, a yellowfin tuna], a tilapia, a sea bream, or a salmon), or reptiles (for example, a soft-shelled turtle).

Examples of the collagen used in the present invention include collagen derived from, for example, a dermis, a tendon, a bone, or a fascia of any of the above-mentioned mammals or the above-mentioned birds, collagen derived from, for example, a skin or a scale of any of the above-mentioned fishes, and collagen derived from, for example, a dermis, a tendon, or a bone of any of the above-mentioned reptiles.

Examples of the atelocollagen used for producing LASCol include atelocollagen that is produced by treating collagen of any of the above-mentioned mammals, birds, fishes, or reptiles with a protease (for example, pepsin), wherein a telopeptide has been partially removed from the amino terminus and/or the carboxyl terminus of the collagen molecule.

Among the above examples, collagen or atelocollagen of a chicken, a pig, a cow, a human, or a rat can be preferably used. More preferably, collagen or atelocollagen of a pig, a cow, or a human can be used as the material for LASCol.

Furthermore, the collagen or atelocollagen of a fish can be used as the material for LASCol. Using a fish allows for obtaining the material easily and safely in a large quantity and providing a degradation product of collagen or atelocollagen (LASCol) that is virus-free and safer to humans.

When collagen or atelocollagen of a fish is used as the material for LASCol, it is preferable to use collagen or atelocollagen of a shark, a carp, an eel, a tuna (for example, a yellowfin tuna), a tilapia, a black bass, a bluegill, a sea bream, or a salmon; and it is more preferable to use collagen or atelocollagen of a tuna, a tilapia, a sea bream, or a salmon.

When atelocollagen is used as the material for LASCol, it is preferable to use atelocollagen that has a heat denaturation temperature of preferably 15° C. or higher, and more preferably 20° C. or higher. For example, when the atelocollagen of a fish is used as the material for the degradation product, it is preferable to use the atelocollagen of a tuna (for example, a yellowfin tuna), a carp, a tilapia, or the like, since such atelocollagen has a heat denaturation temperature of not lower than 25° C.

The above-mentioned arrangement allows for adjusting the temperature at which the therapeutic agent for intervertebral disc degeneration of this embodiment turns into gel to preferably 15° C. or higher, and more preferably 20° C. or higher. Consequently, the above-mentioned arrangement allows for producing a therapeutic agent for intervertebral disc degeneration that is excellent in stability during storage and stability during use.

Such collagen or atelocollagen may be obtained by a well-known method. For example, collagen-rich tissue of a mammal, a bird, or a fish may be put into an acidic solution with a pH of about 2 to 4, thereby eluting collagen. Furthermore, a protease such as pepsin is added to the eluate to partially remove a telopeptide at the amino terminus and/or carboxyl terminus of the collagen molecule. Furthermore, a salt such as sodium chloride may be added to the eluate to precipitate atelocollagen.

LASCol is obtained by allowing an enzyme to act on collagen or atelocollagen, thereby degrading such material. Alternatively, LASCol can also be obtained by producing a degradation product of collagen or atelocollagen (for example, by chemical synthesis or expression of recombinant protein), wherein the degradation product has an already cleaved chemical bond within the triple helical domain.

Hereinafter, a method for obtaining LASCol by degrading the above-mentioned collagen or atelocollagen with an enzyme (for example, protease) will be described.

The enzyme is not limited to any particular one. For example, a cysteine protease is preferably used.

It is preferable to use, as the cysteine protease, a cysteine protease that contains a larger amount of basic amino acids than the amount of acidic amino acids, or a cysteine protease that is active at a hydrogen ion concentration in the acidic range.

Examples of such a cysteine protease may include actinidain [EC 3.4.22.14], papain [EC 3.4.22.2], ficin [EC 3.4.22.3], bromelain [EC 3.4.22.32], cathepsin B [EC 3.4.22.1], cathepsin L [EC 3.4.22.15], cathepsin S [EC 3.4.22.27], cathepsin K [EC 3.4.22.38], cathepsin H [EC 3.4.22.16], alloline, and a calcium dependent protease. The text in square brackets represents an enzyme code number.

Among these, it is preferable to use actinidain, papain, ficin, cathepsin K, alloline, or bromelain, and it is more preferable to use actinidain, papain, ficin, or cathepsin K.

The above-mentioned enzyme can be obtained by a known method. For example, the enzyme can be obtained by producing the enzyme by chemical synthesis; extracting the enzyme from a cell or tissue of a bacterium, a fungus, or various animals and plants; producing the enzyme by a genetic engineering process; or other methods. Needless to say, a commercially available enzyme can also be used.

When collagen or atelocollagen is cleaved by degrading the same with an enzyme (for example, a protease), the cleaving step can be carried out by, for example, any of the methods (i) to (iii) described below. The following methods (i) to (iii) are merely examples of the cleaving step, and the method for producing LASCol is not limited to these methods (i) to (iii).

LASCol-B can be obtained by the following methods (i) and (ii). LASCol-A and LASCol-B can be obtained by the following method (iii).

(i) A method that includes bringing collagen or atelocollagen into contact with an enzyme in the presence of a high concentration of salt.
(ii) A method that includes bringing collagen or atelocollagen into contact with an enzyme that has been in contact with a high concentration of salt.
(iii) A method that includes bringing collagen or atelocollagen into contact with an enzyme in the presence of a low concentration of salt.

Specific examples of the above-mentioned method (i) may include a method that includes bringing collagen or atelocollagen into contact with an enzyme in an aqueous solution containing a high concentration of salt.

Specific examples of the above-mentioned method (ii) may include a method that includes bringing an enzyme into contact with an aqueous solution containing a high concentration of salt in advance and subsequently bringing collagen or atelocollagen into contact with the enzyme.

Specific examples of the above-mentioned method (iii) may include a method that includes bringing collagen or atelocollagen into contact with an enzyme in an aqueous solution containing a low concentration of salt. The specific composition of the above-mentioned aqueous solution is not particularly limited. For example, water can be used.

Although the specific composition of the above-mentioned salt is not particularly limited, a chloride is preferably used. The chloride is not limited to any particular one. For example, NaCl, KCl, LiCl, or $MgCl_2$ can be used.

Although the concentration of the salt in the above-mentioned aqueous solution containing a high concentration of salt is not particularly limited, a higher concentration is more preferable. For example, the concentration is preferably 200 mM or higher, more preferably 500 mM or higher, still more preferably 1000 mM or higher, even more preferably 1500 mM or higher, and most preferably 2000 mM or higher.

Although the concentration of the salt in the above-mentioned aqueous solution containing a low concentration of salt is not particularly limited, a lower concentration is more preferable. For example, the concentration is preferably 200 mM or lower, more preferably 150 mM or lower, still more preferably 100 mM or lower, even more preferably 50 mM or lower, and most preferably substantially 0 mM.

Although collagen or atelocollagen may be dissolved in the above-mentioned aqueous solution (for example, water) in any amount, by way of example, it is preferable that 1 part by weight of collagen or atelocollagen be dissolved in 1000 parts by weight to 10000 parts by weight of the aqueous solution.

The above-mentioned arrangement enables efficient contact between an enzyme and the collagen or atelocollagen when the enzyme is added to the aqueous solution. Consequently, the collagen or atelocollagen can be degraded efficiently with the enzyme.

Although the enzyme may be added to the aqueous solution in any amount, by way of example, it is preferable that 10 parts by weight to 20 parts by weight of the enzyme be added to 100 parts by weight of the collagen or atelocollagen.

The above-mentioned arrangement, in which the concentration of the enzyme in the aqueous solution is high, enables efficient degradation of the collagen or atelocollagen with the enzyme (for example, a protease).

Furthermore, other conditions (for example, the pH of the aqueous solution, temperature, and a contact time) under which the collagen or atelocollagen is brought into contact with the enzyme in the aqueous solution are not particularly limited and may be selected as appropriate. However, these conditions are preferably within the ranges described below. Preferable ranges of these conditions are illustrated below.

1) The pH of the aqueous solution is preferably 2.0 to 7.0, and more preferably 3.0 to 6.5. For keeping the pH of the aqueous solution within the above-mentioned range, a well-known buffer may be added to the aqueous solution. The above-mentioned pH allows the collagen or atelocollagen to be dissolved in the aqueous solution uniformly, and consequently allows the enzymatic reaction to proceed efficiently.

2) The temperature is not limited to any particular value and may be selected depending on the enzyme to be used. The temperature is, for example, preferably 15° C. to 40° C., and more preferably 20° C. to 35° C.

3) The contact time is not limited to any particular length and may be selected depending on the amount of the enzyme and/or the amount of the collagen or atelocollagen. The contact time is, for example, preferably 1 hour to 60 days, more preferably 1 day to 7 days, and even more preferably 3 days to 7 days.

When necessary, at least one step selected from the group consisting of a step of readjusting the pH, a step of inactivating the enzyme, and a step of removing contaminants may be performed after allowing the collagen or atelocollagen to be in contact with the enzyme in the aqueous solution.

The step of removing contaminants can be carried out by a general method for separating a substance. The step of removing contaminants can be carried out by, for example, dialysis, salting-out, gel filtration chromatography, isoelectric precipitation, ion exchange chromatography, or hydrophobic interaction chromatography.

The therapeutic agent for intervertebral disc degeneration according to the present invention is administered into the intervertebral disc, for example, by injection, mainly in a surgical operation. In this case, it is desirable that LASCol contained is the therapeutic agent for intervertebral disc degeneration have an elastic modulus ("practical elastic modulus" described below) not less than a predetermined value. This is because there is a risk that LASCol with a low elastic modulus may flow out from the intervertebral disc.

The therapeutic agent for intervertebral disc degeneration or the material for culturing intervertebral disc cells according to the present invention is provided, for example, in a gel state or a dry state (including powder and a shaped form). The expression. "using the therapeutic agent for intervertebral disc degeneration or the material for culturing intervertebral disc cells according to the present invention at a predetermined concentration" includes a case where instructions to add a certain amount of solvent to LASCol in a dry state are attached to the product or passed on to the user, and in accordance with the instructions, a favorable concentration of LASCol of the present invention is prepared.

"Administration" as used herein means administering a therapeutic agent to a patient via an affected part (intervertebral disc). Furthermore, intervertebral disc disorders treated by using the present invention may include a disease related to intervertebral disc degeneration such as low back pain, spinal canal stenosis, and spinal deformity, in addition to intervertebral disc herniation, which is a typical example. In other words, the present invention can be regarded as a method for treating intervertebral disc degeneration by using the therapeutic agent for intervertebral disc degeneration according to the present invention. Furthermore, the present invention can be regarded as a method for culturing intervertebral disc cells by using the material for culturing intervertebral disc cells according to the present invention.

EXAMPLES

<Preparation of Solution Containing LASCol>

50 mM citric acid buffer solutions (pH 3.0) each containing sodium chloride at a concentration of 0 mM or 1500 mM were prepared. Water was used as a solvent of these aqueous solutions.

For activating actinidain, actinidain was dissolved in 50 mM phosphate buffer (pH 6.5) containing 10 mM dithiothreitol and 5 mM EDTA (Ethylenediaminetetraacetic acid) and the resultant aqueous solution was left to stand at 25° C. for 90 minutes. Note that actinidain had been purified by a well-known method before use (see, for example, Non Patent Literature 1).

Next, pig-derived type I collagen was dissolved in the 50 mM citric acid buffer solution containing the salt) pH 3.0). The resultant solution containing the pig-derived type I collagen was brought into contact with the aqueous solution containing actinidain at 20° C. for 10 days or longer to produce a degradation product of type I collagen. Note that the pig-derived type I collagen had been purified by a well-known method (see, for example, Non Patent Literature 1).

The above-mentioned degradation product was subjected to sodium lauryl sulfate-polyacrylamide gel electrophoresis (SDS-PAGE) to separate the degradation product of type I collagen.

Subsequently, the degradation product of type I collagen was transferred onto a PVDF (polyvinylidene difluoride) membrane by a routine method. Then, an amino acid sequence of the amino terminus of a degradation product of an α1 chain transferred onto the PVDF membrane was determined by the Edman degradation technique.

Note that APRO Science Inc. or Collaborative Laboratory (Analytical tools) of the Faculty of Medicine of Kindai University conducted the actual Edman analysis accordance with a well-known method, at the request of the present inventors.

Table 1 shows the amino acid sequence of the amino terminus and the vicinity thereof of the degradation products of the α1 chain that were obtained at salt concentrations of 0 mM and 1500 mM.

As shown in Table 1, cleavage occurred outside of a triple helical domain represented by "GPMGPSGPRG . . . " when the salt concentration was low (0 mM), while cleavage occurred inside of the triple helical domain when the salt concentration was high (1500 mM). In SEQ ID NO: 3, the triple helical domain starts from glycine (G) that is the third amino acid from the left and extends to the C-terminus. A solution produced in the case of 0 mM is a LASCol-A solution and a solution produced in the case of 1500 mM is a LASCol-B solution. In the following Examples, the LASCol-A solution was used as the LASCol solution.

TABLE 1

| SALT CONCENTRATION [mM] | AMINO-TERMINAL SEQUENCE OF DEGRADATION PRODUCT OF PIG-DERIVED α1 CHAIN | SEQUENCE NUMBER |
|---|---|---|
| 0 | V P G P M G P S G P R G • • • | 3 |
| 1500 | M G P S G P R G • • • | 4 |

In LASCol-A, cleavage also occurs in an α2 chain. In Table 2, SEQ ID NO: 5 represents the amino-terminal portion of the α2 chain. In SEQ ID NO: 5, the triple helical domain starts from glycine (G) located at the left end of ". . . GPMGLMG . . . " and extends to the C-terminus. SEQ ID NO: 6 represents the end of the α2 chain produced at a salt concentration of 0 MM., which is a condition for production of LASCol-A. When compared with SEQ ID NO: 2, SEQ ID NO: 6 corresponds to a sequence resulting from cleavage of a chemical bond between G and $X_3$ in SEQ ID NO: 2.

In other words, in LASCol-A, cleavage in the α1 chain has occurred outside of the triple helical domain, while cleavage in the α2 chain has occurred inside of the triple helical domain. LASCol-A only needs to have either one of cleavages shown in SEQ ID NO: 3 and SEQ ID NO: 6.

TABLE 2

| SALT CONCENTRATION [mM] | AMINO-TERMINAL SEQUENCE OF DEGRADATION PRODUCT OF PIG-DERIVED α2 CHAIN | SEQUENCE NUMBER |
|---|---|---|
| — | • • • G P G P M G LM G P R G P P • • • | 5 |
| 0 | LM G P R G P P • • • | 6 |

FIG. 1 shows an elastic property of a solution containing LASCol (a storage elastic modulus part G' of complex elastic modulus). The horizontal axis represents time (minutes) and the vertical axis represents storage elastic modulus G' (Pa). FIG. 1(a) and FIG. 1(b) have the same horizontal axes but different vertical axes. The scale of the vertical axis in FIG. 1(b) is larger than that of FIG. 1(a). Each curve in FIG. 1(a) and FIG. 1(b) corresponds to the storage elastic moduli of different concentrations of LASCol. LASCol solutions of different concentrations were prepared by using 5 mM hydrochloric acid solution so that the final LASCol concentrations became 2.1 mg/mL, 3.5 mg/mL, and 4.9 mg/mL (FIG. 1(a)), and 21 mg/ml (FIG. 1(b)).

These LASCols are stored in an acidic solution in a temperature range from 5° C. to 10° C. Under this condition, LASCol can be stored in a liquid state. FIG. 1 shows the measurement results of LASCol. For this measurement, a pH adjuster and a concentration adjusting solution were added to LASCol to adjust pH thereof to nearly 7.4, then the LASCol sample was placed in a dynamic viscoelasticity measuring device (rheometer: HAAKE MARS III, Thermo Fisher Scientific Inc.), and the temperature was raised to 37° C. before measurement. The measurement conditions were a frequency of 1 Hz, an amplitude of 6°/second, and a strain percentage of 1%. Raising temperature is completed in a few seconds.

Referring to FIG. 1(a), a storage elastic modulus G' determined immediately after the start of measurement was low regardless of the LASCol concentration. Subsequently, regardless of the LASCol concentration, the storage elastic modulus G' increased and approached a saturation point in about 10 minutes. On the other hand, in FIG. 1(b), a storage elastic modulus G' increased to the saturation point in 1 minute after the start of measurement, and then gradually decreased to saturation level. As is clear from FIG. 1 and FIG. 2, increasing the LASCol concentration shortened the time for the storage elastic modulus G' to increase.

This indicated that the storage elastic modulus G' of the solution containing LASCol increased to a certain value that depended on the LASCol concentration when the pH and concentration of the LASCol solution were adjusted and the temperature thereof was raised. Furthermore, it was found that the storage elastic modulus reached an almost stable value 30 minutes after the LASCol solution was prepared so as to have a predefined concentration and the temperature thereof was raised to 37° C. For this reason, the storage elastic modulus at this time point is referred to as "practical elastic modulus" of LASCol.

It was shown that, when LASCol was exposed to an appropriate condition, the property thereof changed from sol having an unmeasurable elastic modulus to gel having a quantifiable elastic modulus, and thus LASCol could be used as an injectable gel particularly for injection into a living body.

Figure 2:
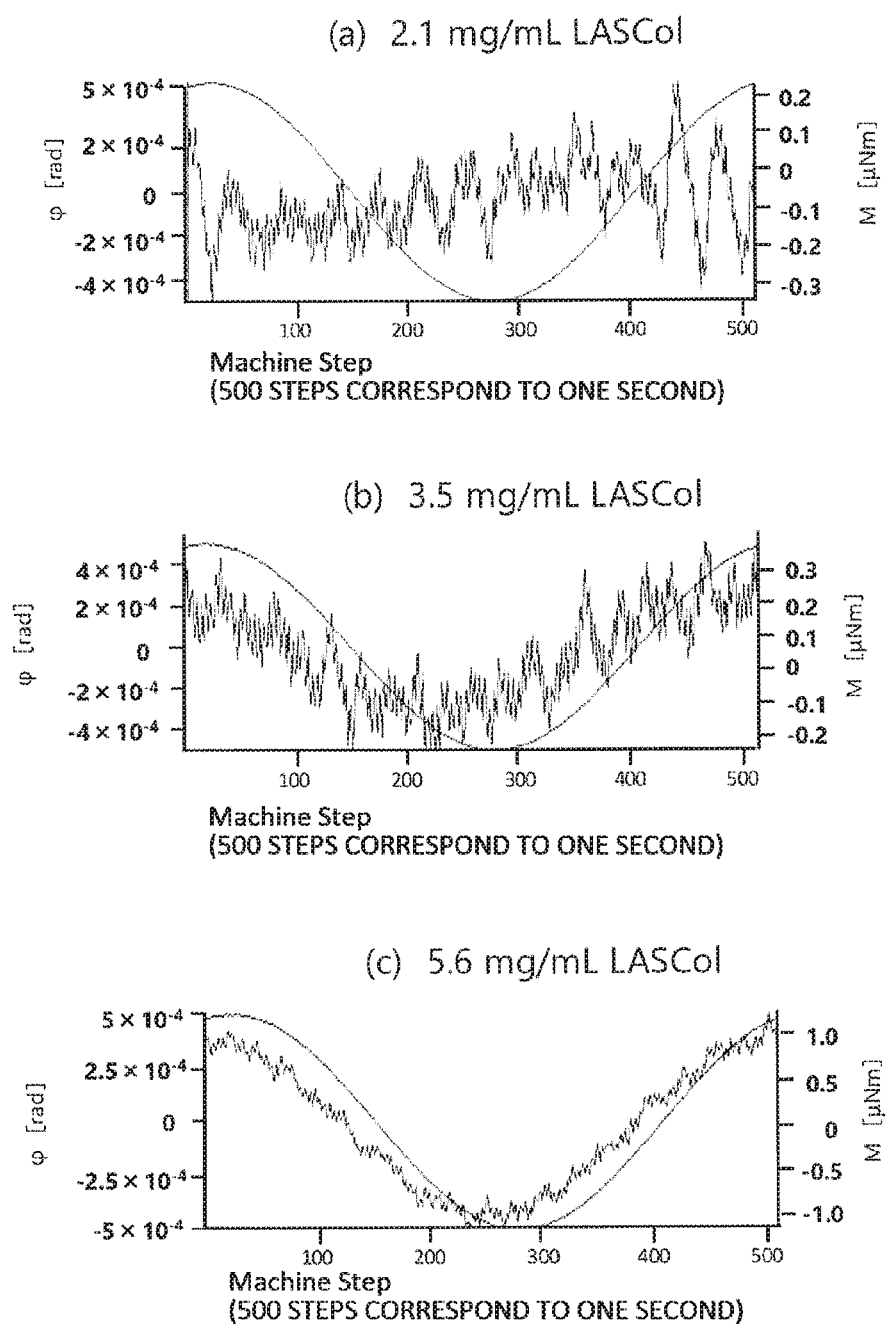
FIG. 2 includes graphs showing the relationship between strain of LASCol and stress.

FIG. 2 represents the relationship between "strain (displacement in a rotation direction of a driving unit of the rheometer)" and "stress (stress received by a receiving unit of the rheometer)" after the LASCol sample was kept in the rheometer for 30 minutes at 37° C. The left vertical axis represents strain $\varphi$ (rad) and the right vertical axis represents stress M ($\mu$Nm). The horizontal axis represents the number of machine steps and is unitless, wherein 500 steps correspond to one second. Thus, the figures in FIG. 2 show the results of measurement during which strain $\varphi$ was changed from $5 \times 10^{-4}$ rad to $-5 \times 10^{-4}$ rad and back again over a period of one second.

FIG. 2(a) represents a case where the LASCol concentration was 2.1 mg/ml, FIG. 2(b) represents a case where the LASCol concentration was 3.5 mg/ml, and FIG. 2(c) represents a case where the LASCol concentration was 5.6 mg/ml. Respective practical elastic moduli were 8 Pa, 20 Pa, and 70 Pa. When the LASCol concentration was 2.1 mg/ml (FIG. 2(a)), little response of stress to strain was observed. Thus, LASCol can be considered to be nearly liquid. When the LASCol concentration was increased to 3.5 mg/ml (FIG. 2(b)), response of stress corresponding to strain was observed.

When the LASCol concentration was further increased (FIG. 2(c)), stress came to synchronize with the applied strain. The reason why the strain and the stress are out of phase is that gel has a loss elastic modulus. Therefore, the present inventors were able to conclude that LASCol turned into gel at a LASCol concentration of 3.5 mg/ml as shown in FIG. 2(b). This concentration was equivalent to a practical elastic modulus of 20 Pa.

When LASCol is used as a therapeutic agent for intervertebral disc degeneration, the lower limit of the storage elastic modulus thereof in a gel form is believed to be 20 Pa. LASCol also functions as a scaffold for cells, and thus needs to stay in one place to some extent. The reason why the lower limit is 20 Pa is that LASCol with an elastic modulus of less than 20 Pa does not behave as gel and thus is believed to have difficulty in staying in the intervertebral disc.

Hereinafter, Examples regarding the therapeutic agent for intervertebral disc degeneration according to the present invention will be described. Note that all the experiments described below were performed with the approval of the Kobe University Medical Ethical Committee and the Kobe University Animal Care and Use Committee.

Samples of a nucleus pulposus and an annulus fibrosus in a human intervertebral disc were removed from a patient by lumbar discectomy or interbody fusion. The number of patients was 15 (n=15). The patients were 46.1±24.1 years old and included 8 men and 7 women. The median score based on Pfirrmann classification was 2, wherein the Pfirrmann classification assesses the level of intervertebral disc degeneration.

Furthermore, nucleus pulposus cells and annulus fibrosus cells in an intervertebral disc of a 12-week-old Sprague-Dawley rat (hereinafter referred to as "SD rat") were also collected.

Then, a 24-well plate on which 7.0 mg/ml LASCol gel was secured and a 24-well plate on which 2.1 mg/ml atelocollagen gel was secured were prepared. The number of cultured cell samples was six (n=6) for both the rat and the human. The samples were cultured for 192 hours in the plates, wherein each plate contains DMEM (Dulbecco's modified Eagle's medium) supplemented with 10% FBS.

Herein, the group of the cells cultured on the LASCol gel is referred to as a LASCol gel group, and the group of the cells cultured on the atelocollagen gel is referred to as an AC gel group.

As a result of cultivation, both human intervertebral disc nucleus pulposus cells and human annulus fibrosus cells proliferated significantly on the atelocollagen gel. On the other hand, it was clear that these cells did not proliferate on the LASCol gel. However, a spheroid, which is a cell aggregate, was observed in larger numbers in the LASCol gel group. FIG. 3 are photographs showing the spheroids formed by the cultured cells.

Reference is made to FIG. 3, FIG. 3(a) shows the spheroids on the LASCol gel, and FIG. 3(b) shows the spheroids on the atelocollagen gel. The scale bar in the photographs represents 100 $\mu$m. In FIG. 3(a), many cells have aggregated densely to form the spheroids (triangular arrow), whereas in FIG. 3(b), only a few cells have aggregated (triangular arrow).

Figure 4:
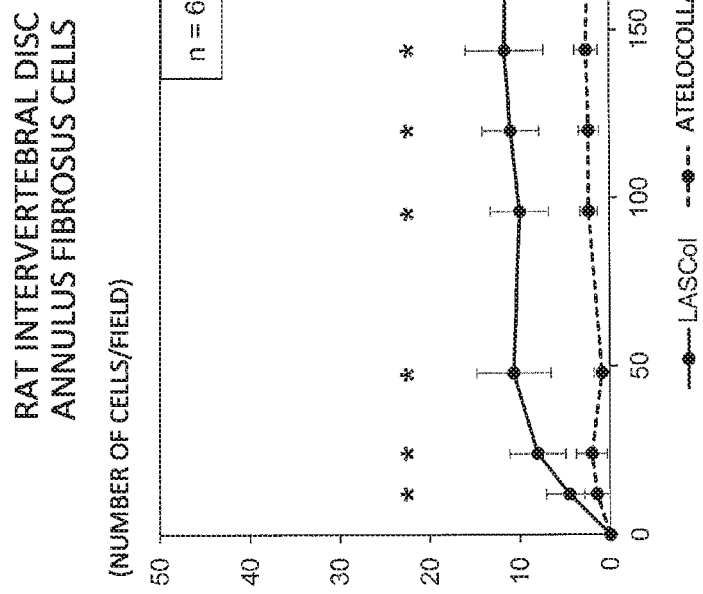
FIGS. 4(a) and 4(b) are graphs showing a change in the number of spheroids over the culture period for the rat intervertebral disc nucleus pulposus cells (FIG. 4(a)) and the rat annulus fibrosus cells (FIG. 4(h)).
Figure 4:
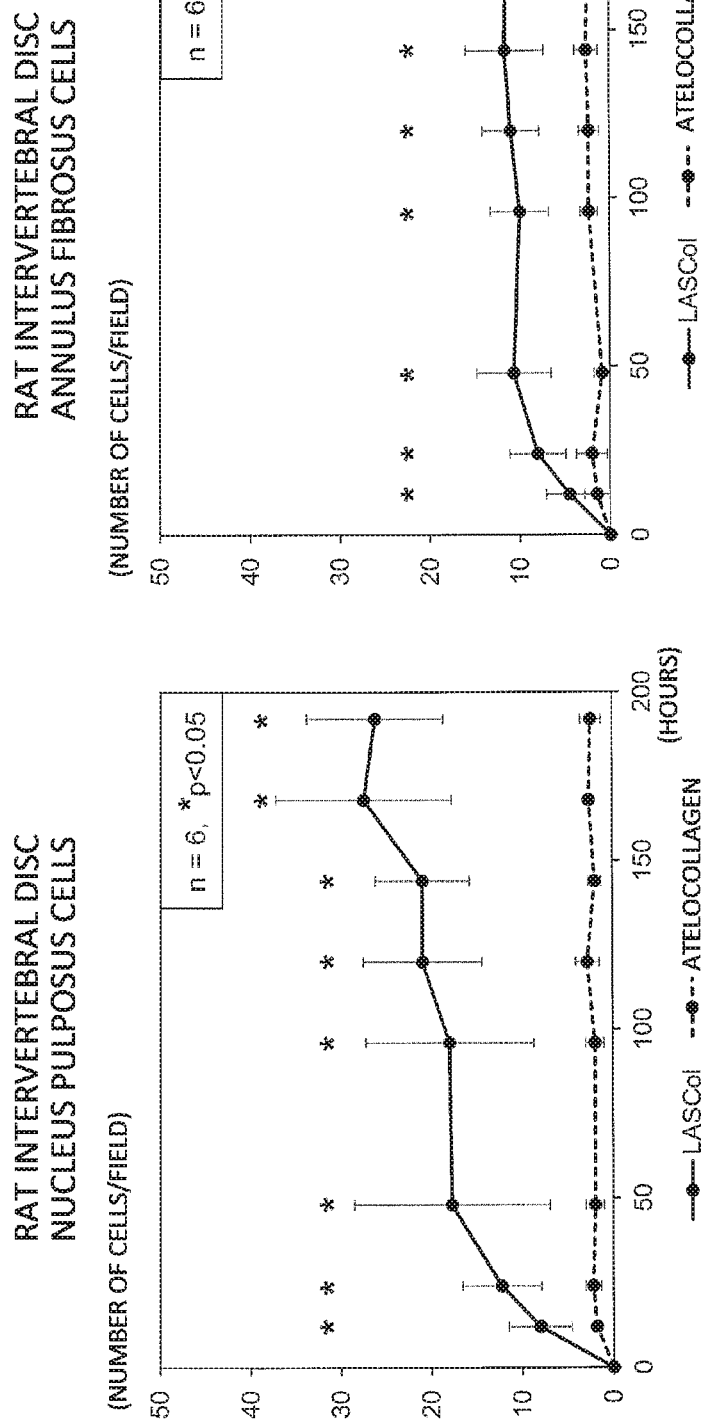
Figure 5:
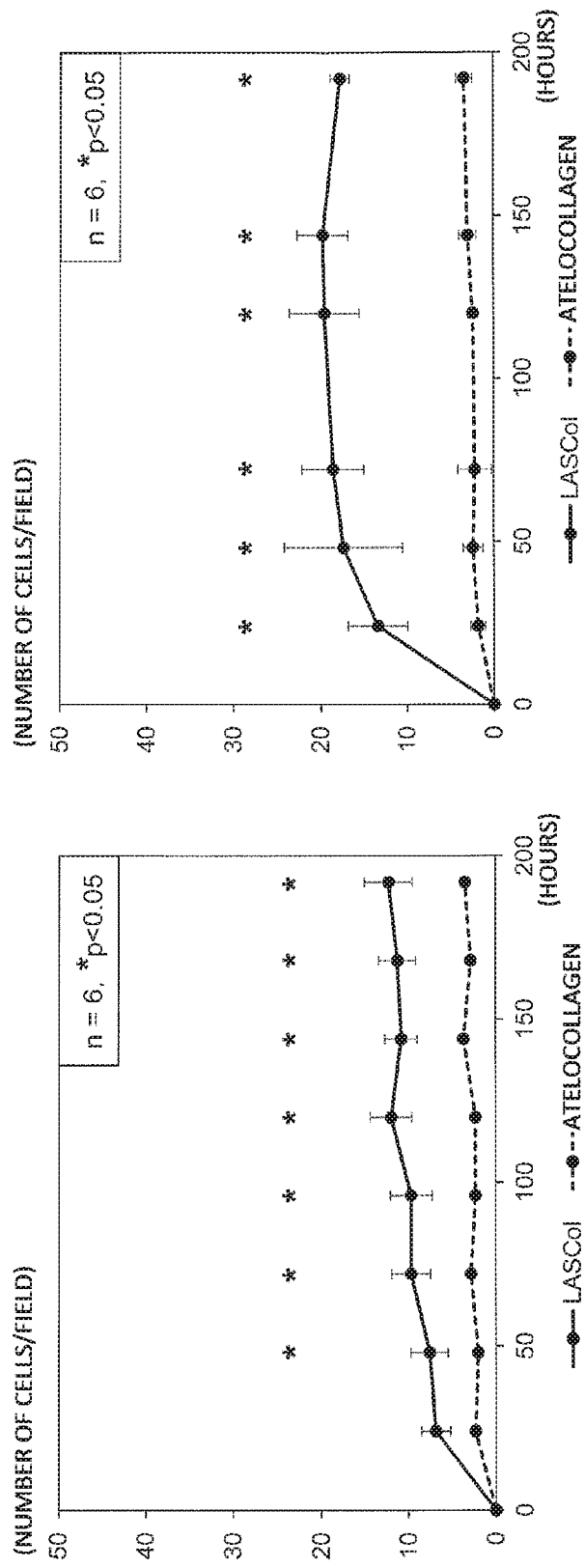
FIGS. 5(a) and 5(b) are graphs showing a change in the number of spheroids over the culture period for the human intervertebral disc nucleus pulposus cells (FIG. 5(a)), and the human annulus fibrosus cells (FIG. 5(b)).

FIG. 4 and FIG. 5 are graphs showing a change in the number of spheroids over the culture period for the rat intervertebral disc nucleus pulposus cells (FIG. 4(a)), the rat annulus fibrosus cells (FIG. 4(b)), the human intervertebral disc nucleus pulposus cells (FIG. 5(a)), and the human annulus fibrosus cells (FIG. 5(b)). In each graph, the horizontal axis represents the culture period (hours) and the vertical axis represents the number of spheroids. In this regard, a spheroid is defined as an aggregate of three or more cells and the number of spheroids was obtained by counting spheroids in a field with a magnification of 100 times.

For example, an aggregate in such a state as indicated by the triangular arrow in FIG. 3(b) was counted as a spheroid. Needless to say, an aggregate of many cells as shown in FIG. 3(a) was regarded as a spheroid. In all the graphs in FIG. 4 and FIG. 5, a solid line represents the LASCol gel group and a dotted line represents the AC gel group. Each graph depicts the mean value±standard deviation. Statistical analysis was performed using a two-way ANOVA with a Tukey-Kramer post-hoc test.

Reference is made to the result for the rat cells in FIG. 4(a) and FIG. 4(b). For both cell types, the spheroids had increased in the LASCol gel group. However, increase of the spheroids was not observed in the AC gel group. The number of spheroids was significantly greater in the LASCol gel group over a period from 12 hours to 192 hours after starting cultivation.

Reference is made to the result for the human cells in FIG. 5(a) and FIG. 5(b). For both cell types, the number of spheroids had increased in the LASCol gel group. However, increase in the number of spheroids was not observed in the AC gel group. The number of spheroids was significantly greater in the LASCol gel group from 48 hours to 192 hours after starting cultivation in the case of the nucleus pulposus cells and from 24 hours to 192 hours in the case of the annulus fibrosus cells.

The above-mentioned results indicate that cell cultivation in the LASCol gel environment leads to a greater number of spheroids and a greater number of cells constituting the spheroids than cultivation in the atelocollagen gel environment. This applied to both the nucleus pulposus cells and the annulus fibrosus cells. As described above, LASCol turned into gel at a LASCol concentration of 3.5 mg/ml or higher (or at a practical elastic modulus of 20 Pa or more). Therefore, it can be stated that LASCol at a concentration of 3.5 mg/ml or higher (at least 7.0 mg/ml) exhibits an ability to support cell culture and spheroid formation in the living body.

Next, multiple immunofluorescence staining of the cultured cells, which included immunostaining each cell phenotype, was performed. For the nucleus pulposus cells, DAPI (4',6-diamidino-2-phenylindole) that binds to DNA, Brachyury serving as a marker of a nucleus pulposus and a notochord, Tie2 serving as a marker of a progenitor cell, and aggrecan, which is an extracellular matrix, were used. For the annulus fibrosus cells, DAPI, PAX1 serving as a marker of the annulus fibrosus, and aggrecan were used.

Figure 6:
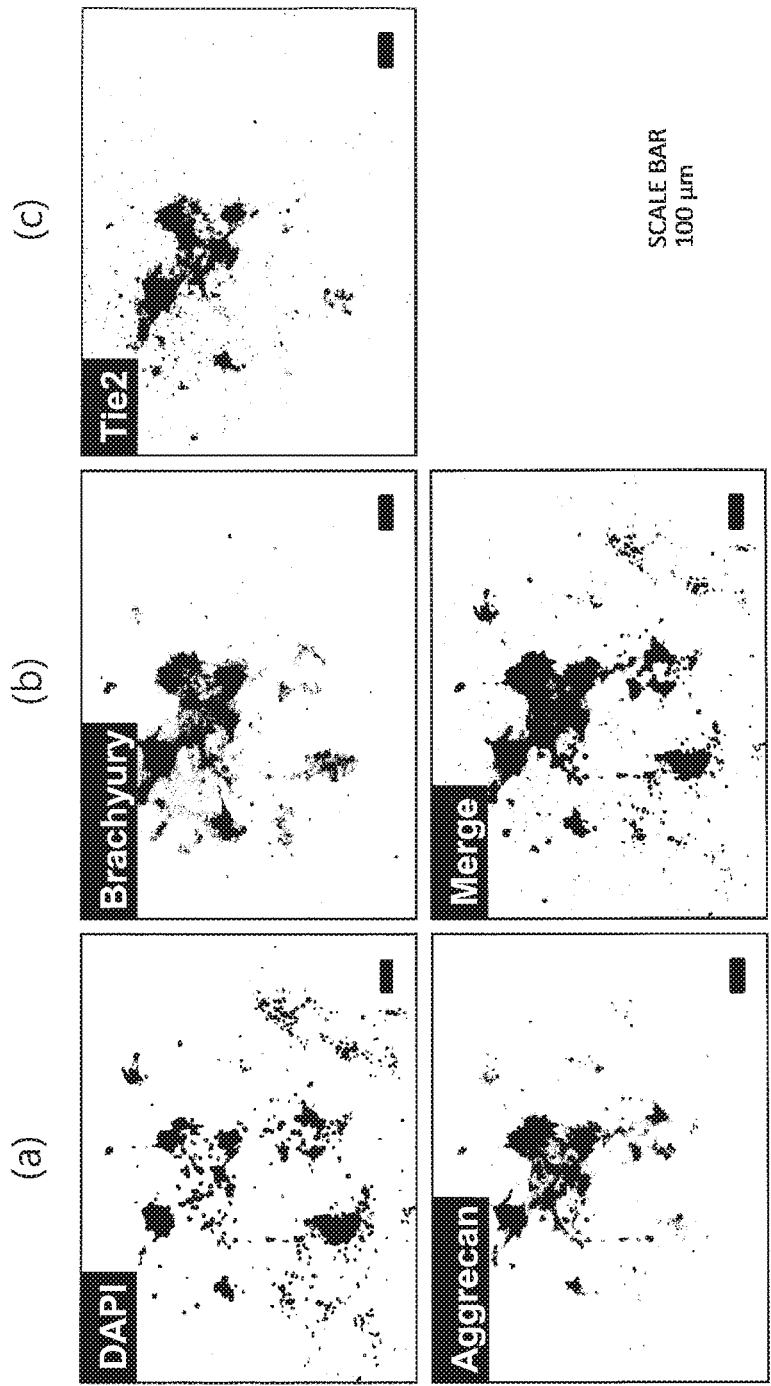
FIG. 6 includes photographs showing the result of staining of a LASCol gel group of human intervertebral disc nucleus pulposus cells cultured on LASCol gel.

FIG. 6 includes photographs showing the result of staining of the LASCol gel group of the human intervertebral disc nucleus pulposus cells. The photographs have been subjected to image processing where only stained regions are colored black and other regions are colored white. Each scale bar at the bottom right represents 100 µm. FIG. 6(a) to FIG. 6(d) correspond to the results for DAPI, Brachyury, Tie2, and aggrecan, respectively. FIG. 6(e) is a photograph obtained by merging all the photographs (indicated as "Merge").

In DAPI staining (FIG. 6(a)), formation of a plurality of spheroids was observed. In staining with Brachyury serving as a marker of a nucleus pulposus and a notochord (FIG. 6(b)), Tie2 serving as a marker of a progenitor cell (FIG. 6(c)), and aggrecan, which constitutes an extracellular matrix (FIG. 6(d)), strong staining corresponding to the spheroids was observed.

Figure 7:
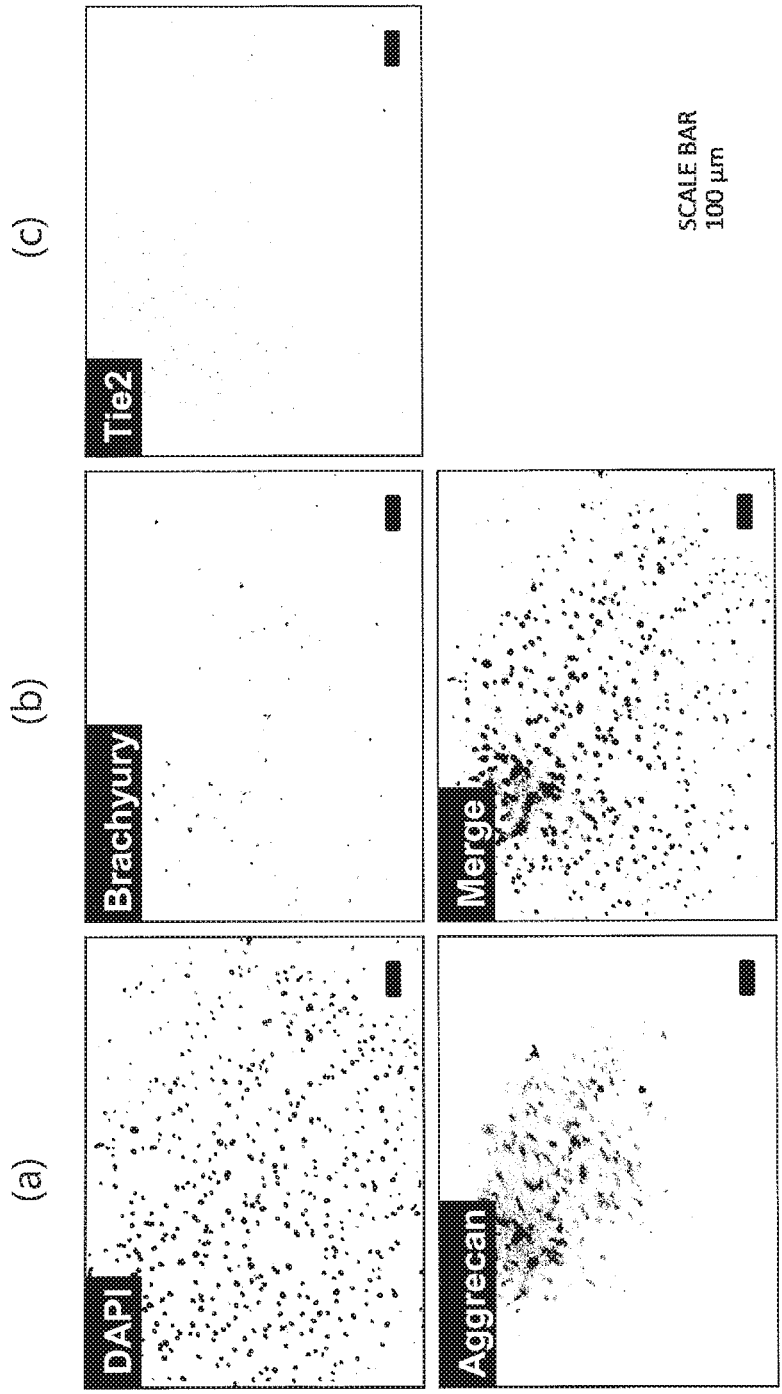
FIG. 7 includes photographs showing the result of staining of an atelocollagen gel group (AC gel group) of human intervertebral disc nucleus pulposus cells cultured on AC gel.

FIG. 7 includes photographs showing the result of staining of the AC gel group of the human intervertebral disc nucleus pulposus cells. As with FIG. 6, the photographs have been subjected to image processing where only stained regions are colored black and other regions are colored white. Each scale bar at the bottom right represents 100 µm. In DAPI staining (FIG. 7(a)), uniform cell distribution was observed. The spheroid formation by aggregated cells as shown in FIG. 6(a) was not observed. In Brachyury staining (FIG. 7(b)) and Tie2 staining (FIG. 7(c)), hardly any staining was observed. In other words, presence of the nucleus pulposus and the notochord, and the progenitor cell was not confirmed. In aggrecan staining (FIG. 7(d)), weak staining corresponding to cell distribution (FIG. 7a)) was observed.

Figure 8:
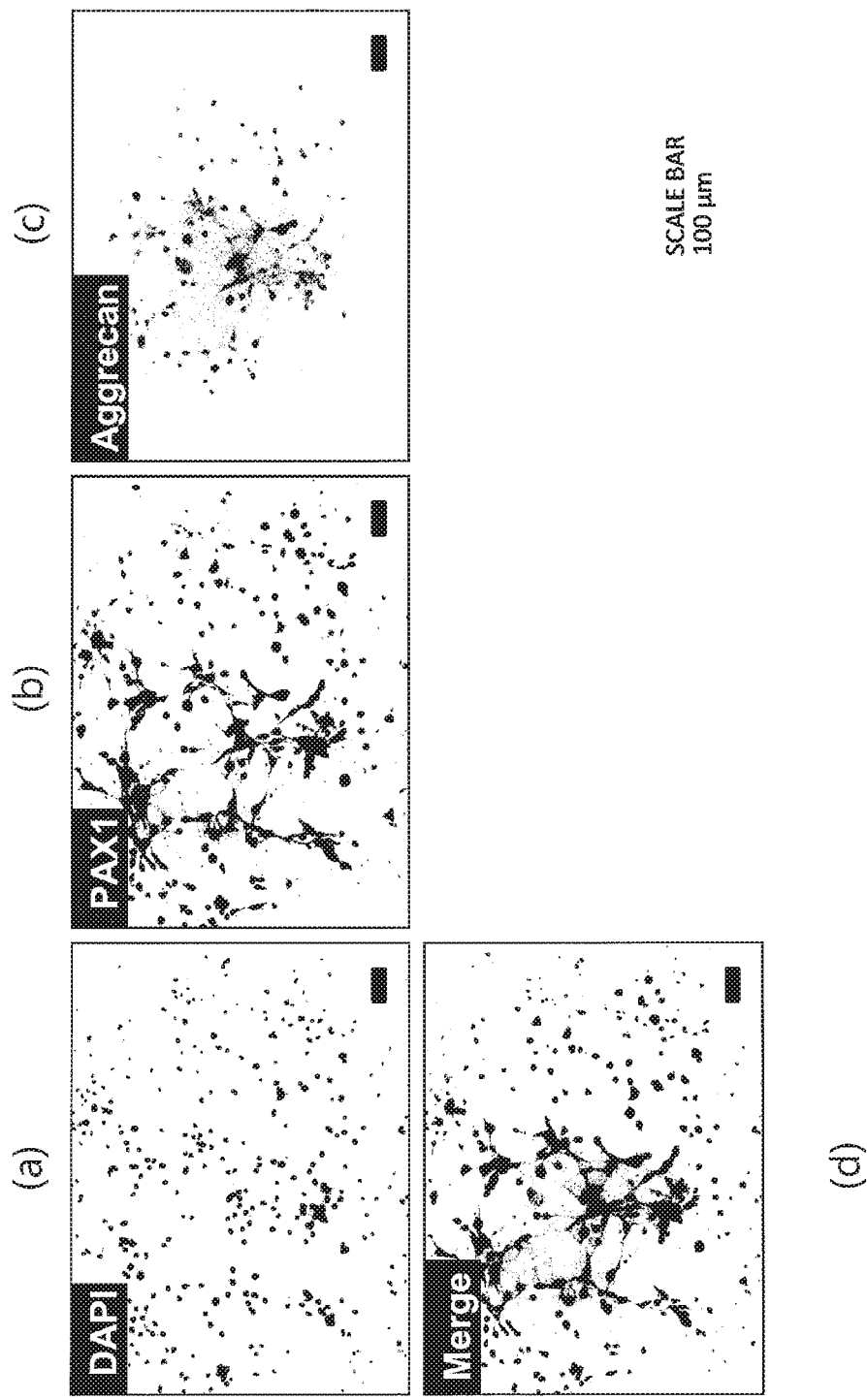
FIG. 8 includes photographs showing the result of staining of the LASCol gel group of human intervertebral disc annulus fibrosus cells.

FIG. 8 includes photographs showing the result of staining of the LASCol gel group of the human intervertebral disc annulus fibrosus cells. As with FIG. 6, the photographs have been subjected to image processing where only stained regions are colored black and other regions are colored white. Each scale bar at the bottom right represents 100 µm. In DAPI staining (FIG. 8(a)), formation of a plurality of spheroids was observed. In staining with PAX1 serving as a marker of the annulus fibrosus (FIG. 8(b)) and staining with aggrecan (FIG. 8(c)), strong staining corresponding to the spheroids (FIG. 8(a)) was observed.

Figure 9:
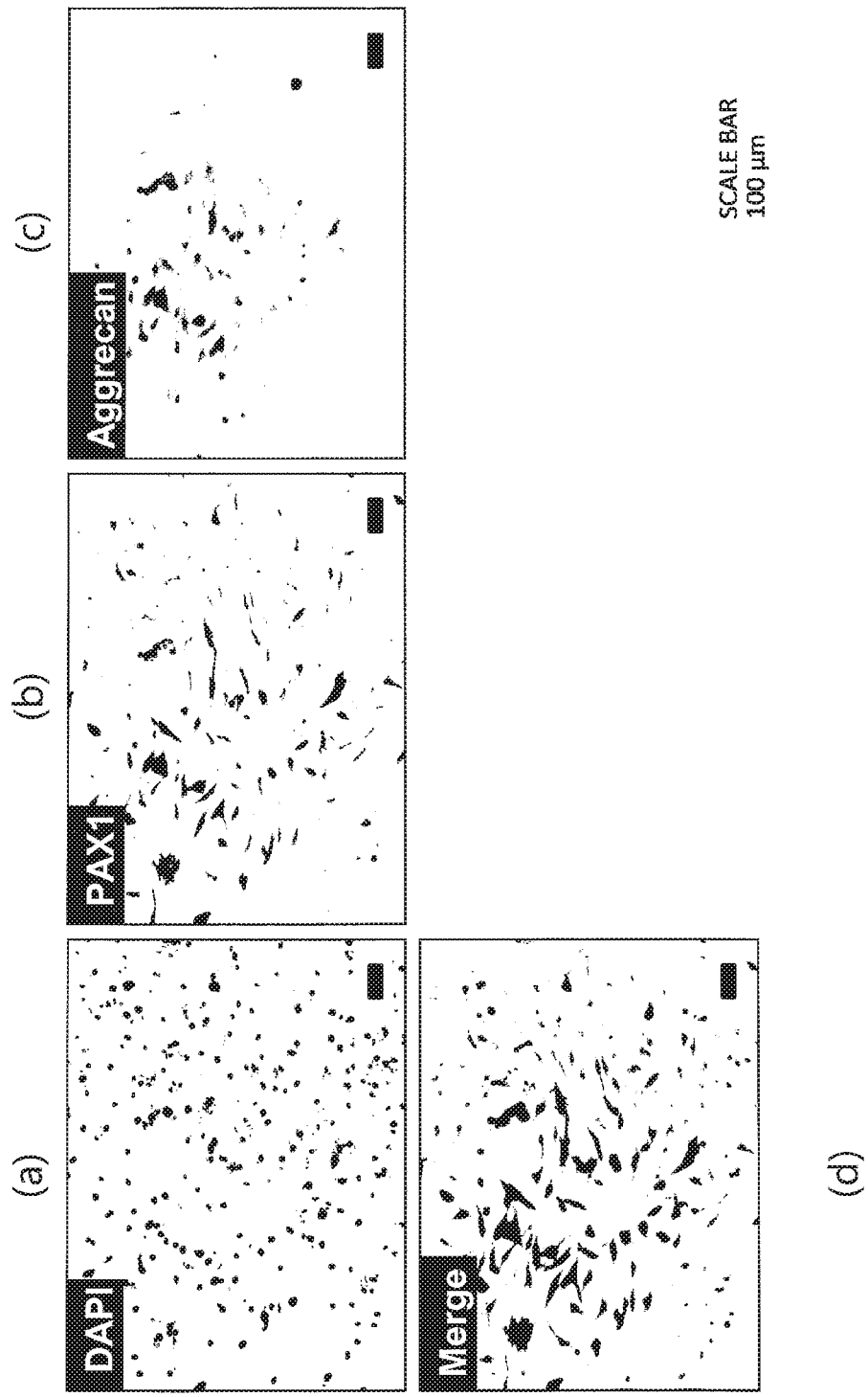
FIG. 9 includes photographs showing the result of staining of the AC gel group of the human intervertebral disc annulus fibrosus FIG. 10 (a) is a roentgenogram and FIG. 10(b) is a photograph of an MRI T2-weighted image of a rat tail where a test for maintenance of a distance between vertebrae was conducted.

FIG. 9 includes photographs showing the result of staining of the AC gel group of the human intervertebral disc annulus fibrosus cells. As with FIG. 6, the photographs have been subjected to image processing where only stained regions are colored black and other regions are colored white. Each scale bar at the bottom right represents 100 µm. In DAPI staining (FIG. 9(a)), uniform cell distribution was observed but spheroid formation was not observed. In staining with PAX1 serving as a marker of the annulus fibrosus (FIG. 9(b)) and staining with aggrecan (FIG. 9(c)), weak staining corresponding to cell distribution (FIG. 9(a)) was observed.

The above results indicate the following: LASCol promotes spheroid formation of the nucleus pulposus cells and the annulus fibrosus cells, thereby leading to migration, infiltration, and settlement of the nucleus pulposus cells, the progenitor cells, and the annulus fibrosus cells, which regenerate tissue; and consequently, the tissue-specific extracellular matrix (aggrecan) appears. In contrast, when atelocollagen is used, although the number of cells increases, the nucleus pulposus cells, the progenitor cells, and the annulus fibrosus cells can be hardly detected and the extracellular matrix of the tissue hardly appears. Accordingly, LASCol can be used as a culture material that maintains and further enhances the functions of the nucleus pulposus cell and the annulus fibrosus cell.

This indicates that regenerating the nucleus pulposus cell, the progenitor cell, and the annulus fibrosus cell while maintaining the intervertebral space can be expected by using LASCol in admixture with an auxiliary substance, even if the intervertebral space-maintaining ability of LASCol alone is poor. Examples described below illustrate that LASCol can actually allow a cell that produces proteoglycan, a component of a nucleus pulposus, to migrate from surrounding cells and to infiltrate into an intervertebral space from which nucleus pulposus cells have been removed.

Next, the result of in vivo experiments using rats is described. Twelve-week-old SD rats were used for the experiment. A small incision was made on the tail skin of an SD rat under general anesthesia and the nucleus pulposus was removed from the intervertebral discs between the 8th and the 9th, the 9th and the 10th, and the 10th and the 11th caudal vertebrae. Subsequently, 15 µl of 21.0 mg/ml LASCol, 7.0 mg/ml atelocollagen, and a solvent as control were injected into the nucleus pulposus-removed region of the respective intervertebral discs. The small incision was sutured with nylon thread.

Then, plain X-ray images were taken 0, 7, 14, 28, and 56 days after operation. A value obtained by correcting a distance between vertebrae for a preoperative value (% Disc Height Index, hereinafter referred to as "% DHI") was calculated by using the method of Masuda et al. (Non-Patent Literature 2). Groups injected with LASCol, atelocollagen, and the solvent are designated as a LASCol-receiving group, an AC-receiving group, and a control group, respectively.

Figure 10:
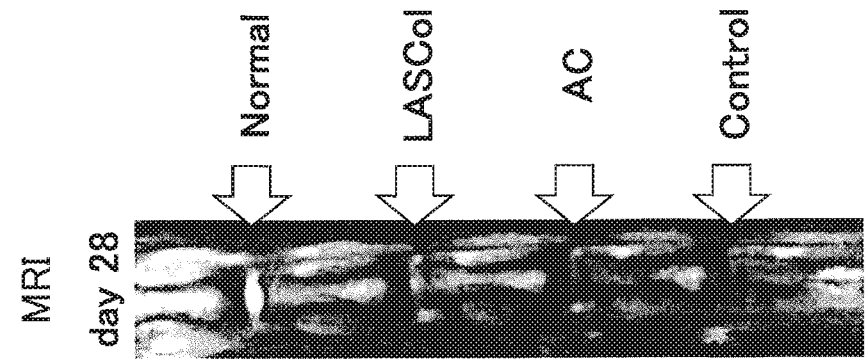
Figure 10:
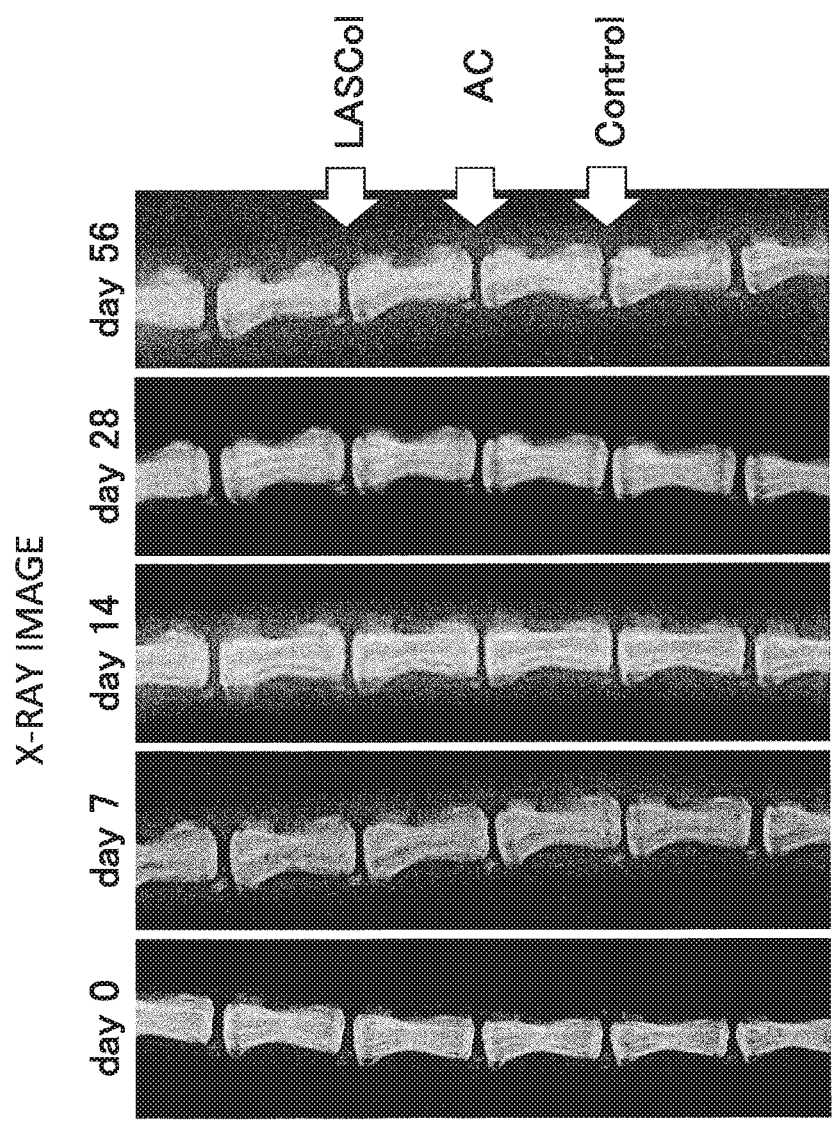

FIG. 10 illustrates a plain x-ray image (FIG. 10(a)) and a 12-weighted image of MRI (Magnetic Resonance Imaging) (FIG. 10(b)), wherein MRI was performed four weeks after operation. FIG. 10(a) is a set of plain x-ray images that were taken after the operation on the days indicated in the figure. The arrows indicate places to which LASCol (between the eighth and the ninth caudal vertebrae), atelocollagen (labeled as "AC," between the ninth and the tenth caudal vertebrae), and the control (labeled as "Control," between the tenth and the eleventh caudal vertebrae) were administered.

Reference is made to FIG. 10(b). In the MRI T2-weighted image, all of the LASCol-receiving group, the AC-receiving group, and the control group showed a lower brightness compared to a normal intervertebral disc (labeled as "Normal" in FIG. 10(b)). However, the LASCol-receiving group showed a higher brightness compared to the AC-receiving group and the control group. This indicates that degeneration after removal of the nucleus pulposus is reduced in the LASCol-receiving group compared to the AC-receiving group and the control group.

Figure 11:
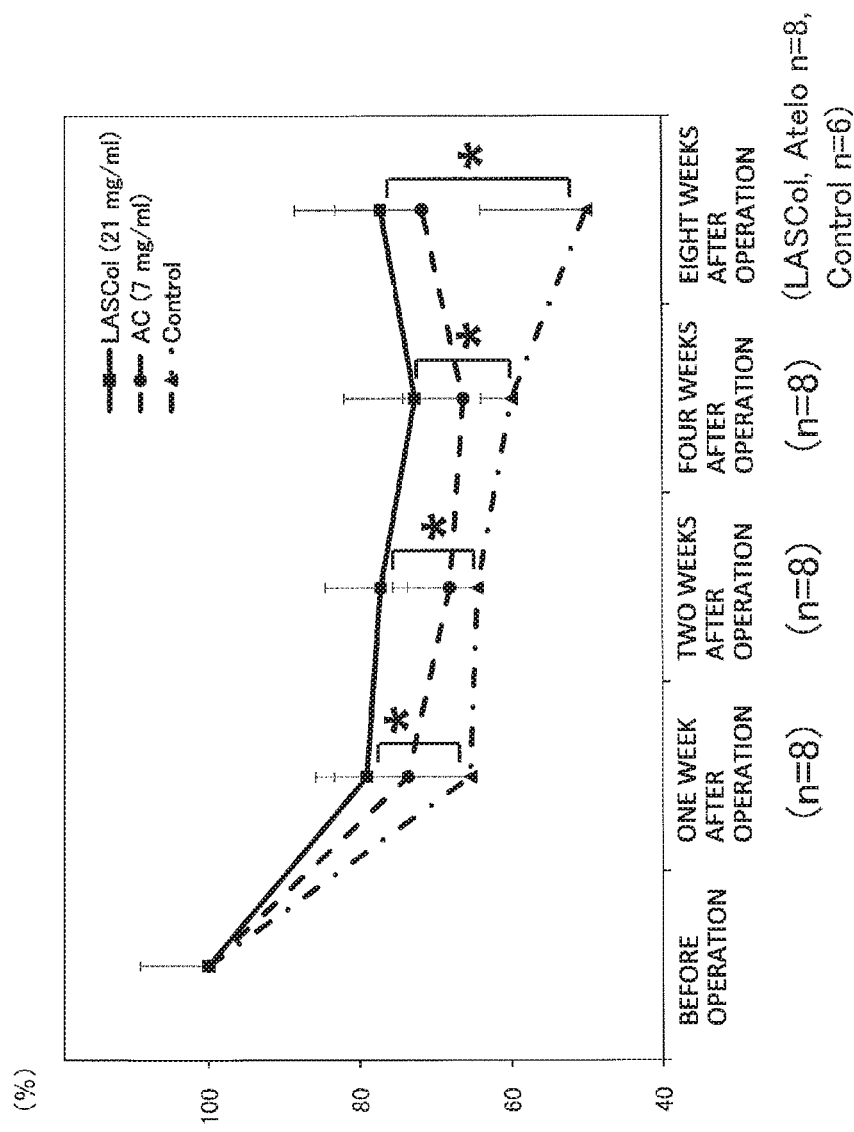
FIG. 11 is a graph showing the result of the test for maintenance of the distance between vertebrae using the rat.

FIG. 11 is a graph showing % DHI calculated from the plain x-ray images versus time after operation. Referring to FIG. 11, the horizontal axis represents time after operation (time in weeks after operation) and the vertical axis represents % DHI. The % DHI values for one week after operation, two weeks after operation, and four weeks after operation are based on the data with a sample size of 8 (n=8). The % DHI values for eight weeks after operation are based on the data with a sample size of 8 (n=8) in the LASCol-receiving group and the AC-receiving group, and 6 (n=6) in the control group.

Referring to FIG. 11, in all the groups, % DHI decreased until seven days after operation. However, regarding the extent of decrease, % DHI for the LASCol group stopped decreasing at a significantly higher level than the control group. No significant difference was observed between the LASCol-receiving group and the AC-receiving group or between the AC-receiving group and the control group. Thereafter, % DHI for all the LASCol-receiving group, the AC-receiving group, and the control group showed tendency to decrease.

Next, the effect of different concentrations of LASCol on % DHI was examined. 7 mg/ml, 14 mg/ml, 21 mg/ml, and 42 mg/ml LASCol samples were prepared as samples having different concentrations. For comparison, 7 mg/ml atelocollagen and a solvent control were also prepared.

Rats treated with 7 mg/ml LASCol were designated as "7 mg LASCol-receiving group," rats treated with 14 mg/ml LASCol were designated as "14 mg LASCol-receiving group," rats treated with 21 mg/ml LASCol were designated as "21 mg LASCol-receiving group," and rats treated with 42 mg/ml LASCol were designated as "42 mg LASCol-receiving group." Rats treated with 7 mg/ml atelocollagen were designated as 7 mg AC-receiving group.

Figure 12:
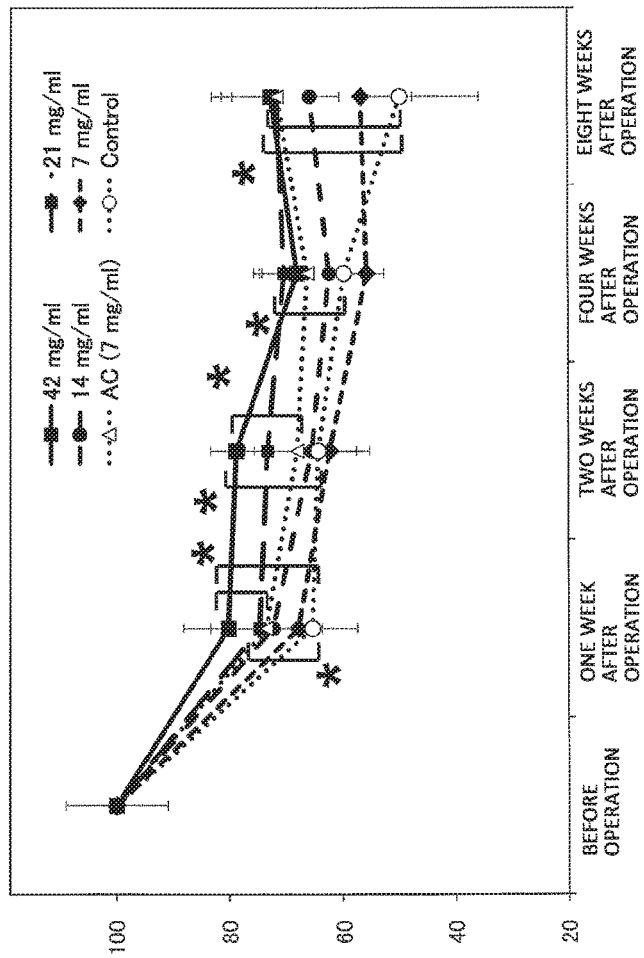
FIG. 12 is a graph showing the effect of different concentrations of LASCol on the distance between vertebrae (° % DHI).

The results are shown in FIG. 12(a). The horizontal axis represents time after operation (time in weeks after operation) and the vertical axis represents % DHI. The number of rats used in each group is shown in FIG. 12(b). At eight weeks after operation, the 42 mg LASCol-receiving group, the 21 mg LASCol-receiving group, and the 7 mg AC-receiving group showed a significantly higher % DHI value than the control group. This indicates that LASCol alone at 21 mg/ml or higher has an intervertebral space-maintaining ability.

Next, the effect of addition of a growth factor to LASCol was examined. Cell regeneration in the nucleus pulposus region can be expected by adding the growth factor. LASCol to which OP-1 (Osteogenic Protein-1) was added as the growth factor was prepared. Besides OP-1, a growth factor such as bFGF, TGF-β1, GDF-5, BMP2, VEGF, or IGF-1 may be used. Regarding the OP-1 concentration, 2 μg of OP-1 was mixed with 15 μl of 21 mg/ml LASCol. The group that received this mixture was designated as OP-1+LASCol-receiving group.

Figure 13:
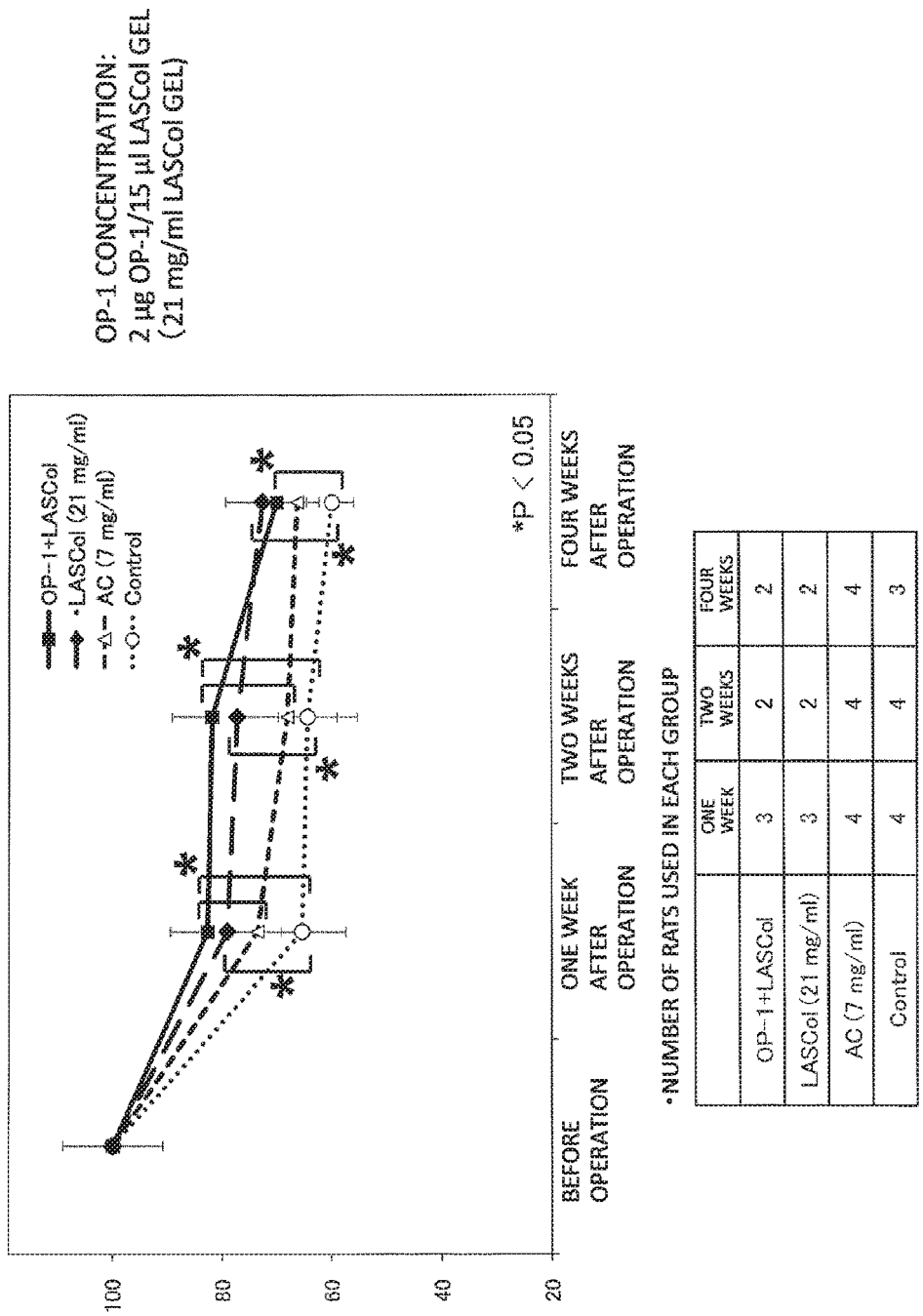
FIG. 13 is a graph showing the effect of addition of a growth factor to LASCol.

FIG. 13(a) shows % DHI for the OP-1+LASCol-receiving group, the 21 mg LASCol-receiving group, the 7 mg AC-receiving group, and the control group. The horizontal axis represents time in weeks after operation and the vertical axis represents % DHI. The number of rats used in each group is shown in FIG. 13(b).

Referring to FIG. 13(a), both the OP-1+LASCol-receiving group and the 21 mg LASCol-receiving group showed a significantly higher % DHI than the control group during the four weeks after the operation. This result also supports that LASCol alone at 21 mg/ml or higher has an intervertebral space-maintaining ability equal to or higher than atelocollagen.

Accordingly, LASCol at 21 mg/ml or higher is considered to be favorable when LASCol is applied alone to a human as the therapeutic agent for intervertebral disc degeneration.

Since the amount of LASCol administered to the nucleus pulposus region of the rat tailbone is very small (15 μl), a concentration of 42 mg/ml is close to the upper limit of a working concentration. However, when LASCol is applied to a human, a higher concentration of LASCol including one in a dry state can be presumably used by modifying, for example, the method and/or mode of administration.

Figure 15:
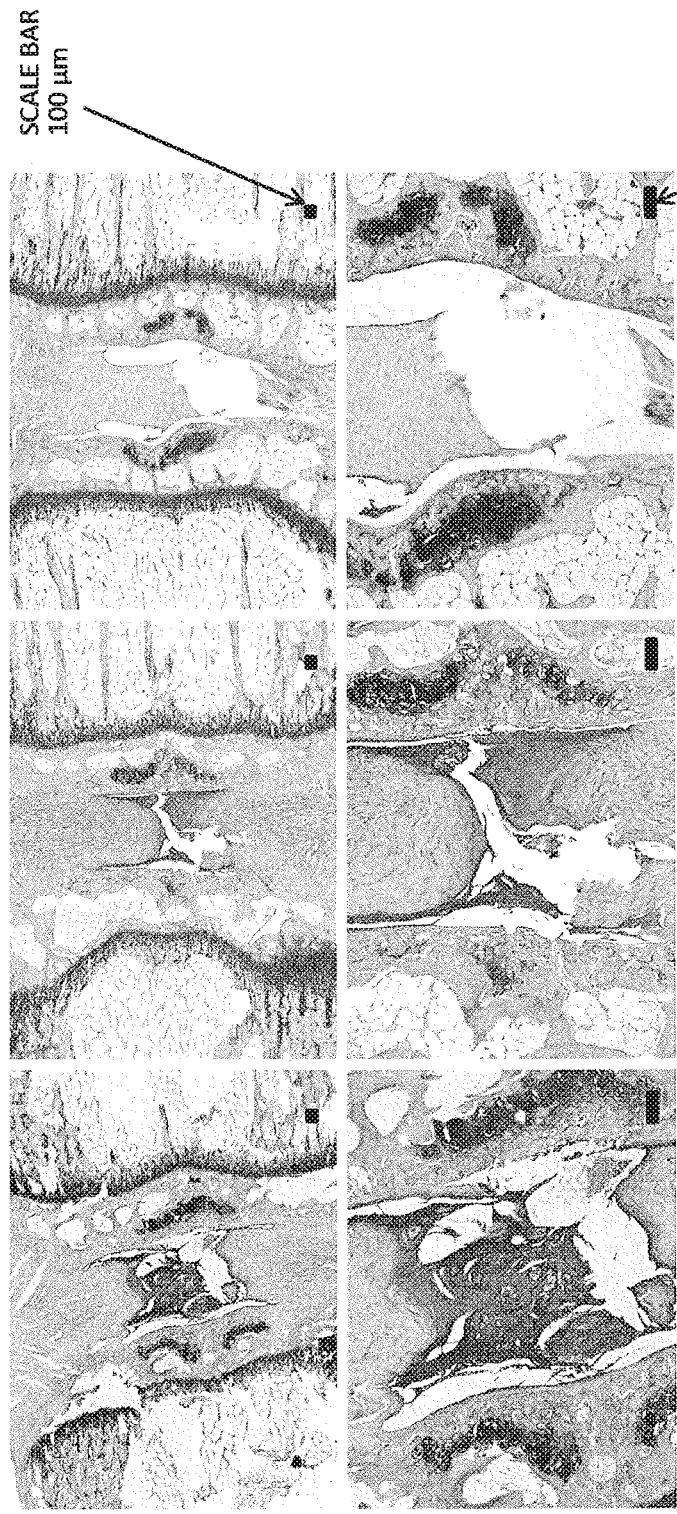
FIG. 15 includes photographs showing a tissue specimen of the nucleus pulposus region of a rat caudal vertebra that was stained with safranin O two weeks after operation.
Figure 16:
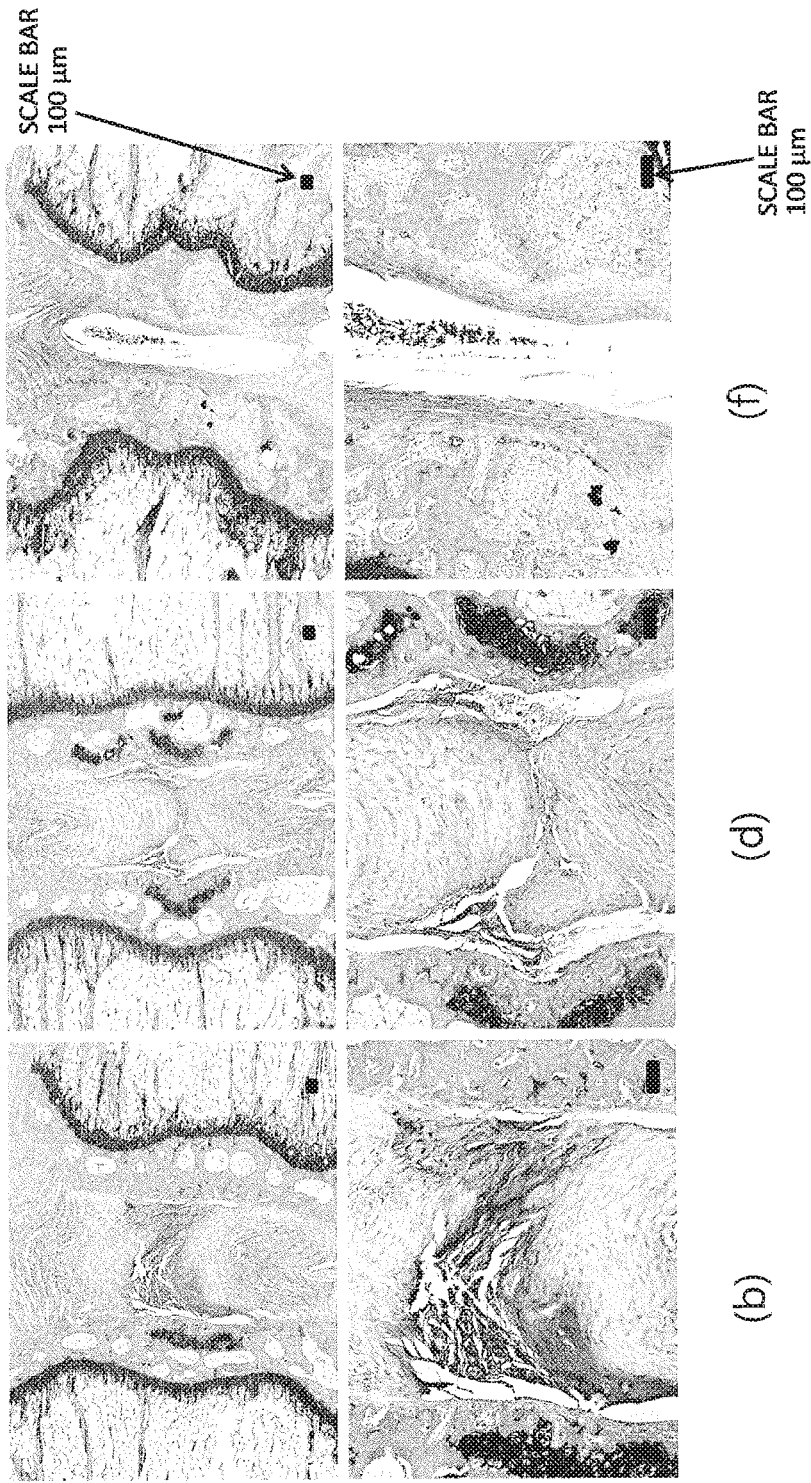
FIG. 16 includes photographs showing a tissue specimen of the nucleus pulposus region of a rat caudal vertebra that was stained with safranin O four weeks after operation.
Figure 17:
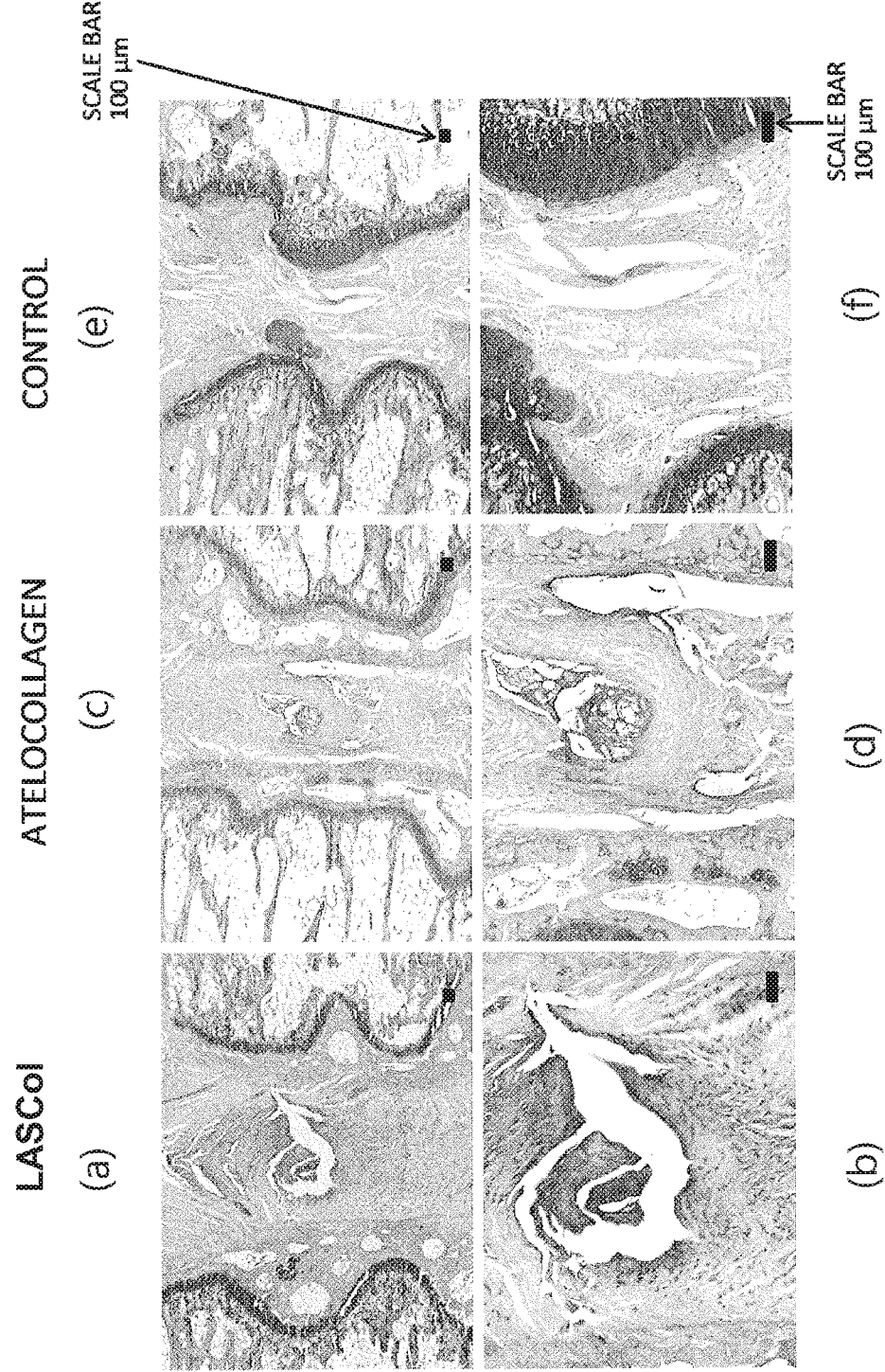
FIG. 17 includes photographs showing a tissue specimen of the nucleus pulposus region of a rat caudal vertebra that was stained with safranin O eight weeks after operation.

FIG. 14 includes photographs showing a tissue specimen of the nucleus pulposus region of a rat caudal vertebra that was stained with safranin O one week after operation. More specifically, an intervertebral disc of a rat tail and caudal vertebrae on either side of the intervertebral disc were removed, fixed with formalin, embedded in paraffin, sectioned, and stained with safranin O. Proteoglycan, which is a representative extracellular matrix, is stained red with safranin O. Each photograph in FIG. 14 is a photograph obtained by image processing that converted a photograph of staining into a black-and-white one. Each photograph shows a specimen of the space between the caudal vertebrae, the caudal vertebrae being located on the left and right sides in the photograph. The caudal vertebrae and the nucleus pulposus region are indicated in FIG. 14(e). Other photographs in FIG. 14 and photographs shown below in FIG. 15 to FIG. 17 are also the same as described above.

FIG. 14(a) and FIG. 14(b) show the cases where the nucleus pulposus region (a region where nucleus pulposus originally existed) was filled with 21 mg/ml LASCol after the nucleus pulposus of the rat caudal vertebra was removed (these represent LASCol-receiving groups). FIG. 14(c) and FIG. 14(d) show the cases where the nucleus pulposus region was filled with 7 mg/ml atelocollagen (these represent AC-receiving groups). FIG. 14(e) and FIG. 14(f) show the cases where the nucleus pulposus region was filled with the solvent (in FIG. 14, this is indicated as "control").

The scale bar at the bottom right in each photograph represents 100 μm. FIG. 14(a) and FIG. 14(b), FIG. 14(c) and FIG. 14(d), and FIG. 14(e) and FIG. 14(f) are pairs of photographs of the same part taken at different magnifications. The scale bars were shown in FIG. 14(e) and FIG. 14(f). Other photographs in FIG. 14 and photographs shown below in FIG. 15 to FIG. 17 are also the same as described above.

Referring to FIG. 14(a) and FIG. 14(b), in the case of LASCol administration, a densely red-stained part and a proteoglycan-rich area (arrowhead) were observed in the nucleus pulposus region. Additionally, cell infiltration was observed in the proteoglycan-rich area.

Referring to FIG. 14(c) and FIG. 14(d), in the case of atelocollagen administration, a red-stained part (arrowhead) was also observed in the nucleus pulposus region. However, the color tone was lighter compared to the case of LASCol administration shown in FIG. 14(a) and FIG. 14(b), and only a little cell infiltration was observed.

Referring to FIG. 14(e) and FIG. 14(f), in the case of solvent administration, no red-stained part or cell was observed in the nucleus pulposus region.

FIG. 15, FIG. 16, and FIG. 17 are photographs showing a tissue specimen of the nucleus pulposus region of the rat caudal vertebra that was stained with safranin O two weeks after operation, four weeks after operation, and eight weeks after operation, respectively. In each set of the photographs, (a) and (b) show the cases where the nucleus pulposus region was filled with LASCol after the nucleus pulposus of the rat caudal vertebra was removed. (c) and (d) show the cases where the nucleus pulposus region was filled with atelocollagen. (e) and (f) show the cases where the nucleus pulposus region was filled with the solvent (indicated as "control" in each figure).

Referring to FIG. 17(a) and FIG. 17(b), in the case of LASCol administration, the nucleus pulposus region was densely stained red. This indicates abundance in proteoglycan. Cell infiltration into the nucleus pulposus region was also confirmed.

Referring to FIG. 17(c) and FIG. 17(d), in the case of atelocollagen administration, a red-stained part was also observed in the nucleus pulposus region. However, the color tone was lighter compared to the case of LASCol administration shown in FIG. 17(a) and FIG. 17(b), and only a little cell infiltration was observed.

Referring to FIG. 17(e) and FIG. 17(f), in the case of solvent administration, no red-stained part or cell was observed in the nucleus pulposus region. Accordingly, the result obtained was almost the same as that obtained one week after operation.

Figure 18:
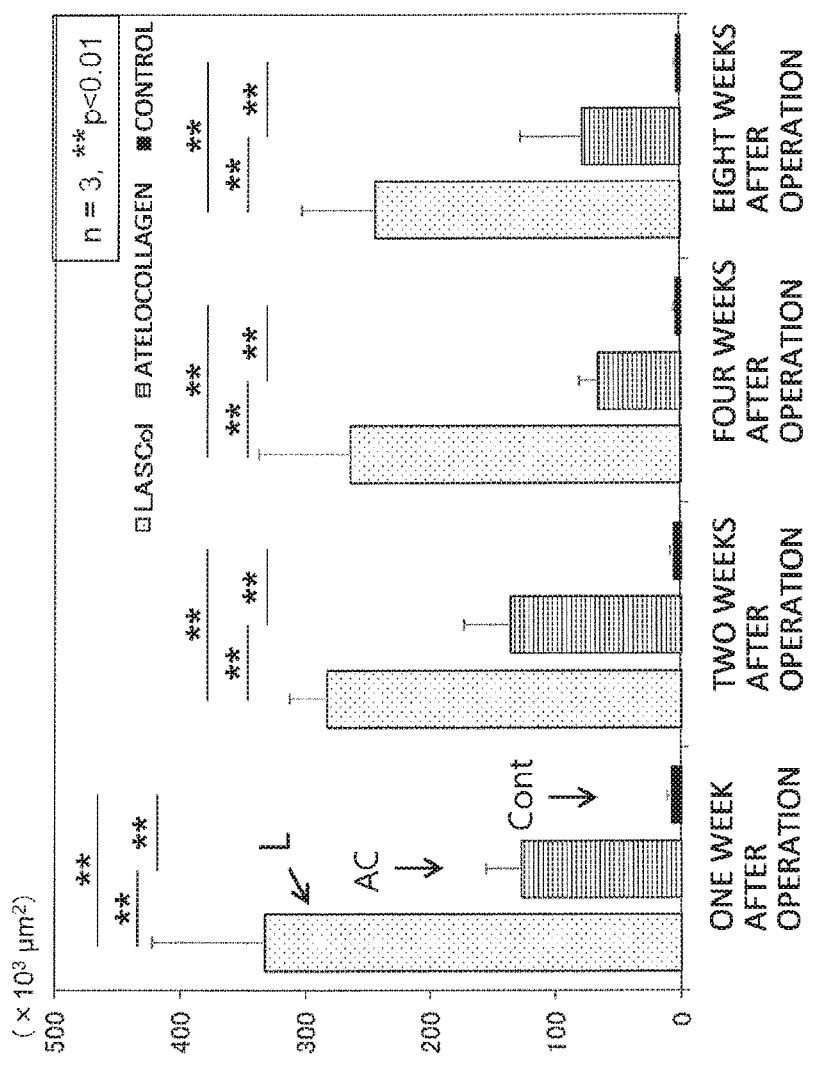
FIG. 18 is a graph showing the result of measuring the area of red parts indicative of proteoglycan positivity (safranin O positivity) in FIGS. 14 to 17 at specified weeks after operation.

FIG. 18 shows the result of more quantitative analysis of FIG. 14 to FIG. 17. The horizontal axis represents time in weeks after operation and the vertical axis represents the area of the red part ($\times 10^3$ $\mu m^2$) positive for proteoglycan. The results for the LASCol-receiving group, the AC-receiving group, and the control group at specified weeks after operation are shown side by side. In the part for one week after operation, the LASCol-receiving group was labeled as "L," the atelocollagen-receiving group was labeled as "AC," and the control group was labeled as "Cont."

The areas one week after operation for the LASCol group, the atelocollagen group, and the control group were $(3.33\pm0.89)\times10^5$ $\mu m^2$, $(1.27\pm0.29)\times10^5$ $\mu m^2$, and $(7.47\pm3.67)\times10^3$ $\mu m^2$, respectively. The areas two weeks after operation were $(2.83\pm0.30)\times10^5$ $\mu m^2$, $(1.36\pm0.37)\times10^5$ $\mu m^2$, and $(5.03\pm2.70)\times10^3$ $\mu m^2$, respectively. The areas four weeks after operation were $(2.64\pm0.73)\times10^5$ $\mu m^2$, $(6.55\pm1.53)\times10^4$ $\mu m^2$, and $(3.50\pm1.39)\times10^3$ $\mu m^2$, respectively. The areas eight weeks after operation were $(2.44\pm0.59)\times10^5$ $\mu m^2$, $(7.80\pm5.03)\times10^4$ $\mu m^2$, and $(2.52\pm1.68)\times10^3$ $\mu m^2$, respectively.

At all the time points, the LASCol-receiving group showed a significantly larger area than the other two groups, and the atelocollagen-receiving group showed a significantly larger area than the control group. Furthermore, no significant change was seen in any of the groups from one to eight weeks after operation.

Figure 19:
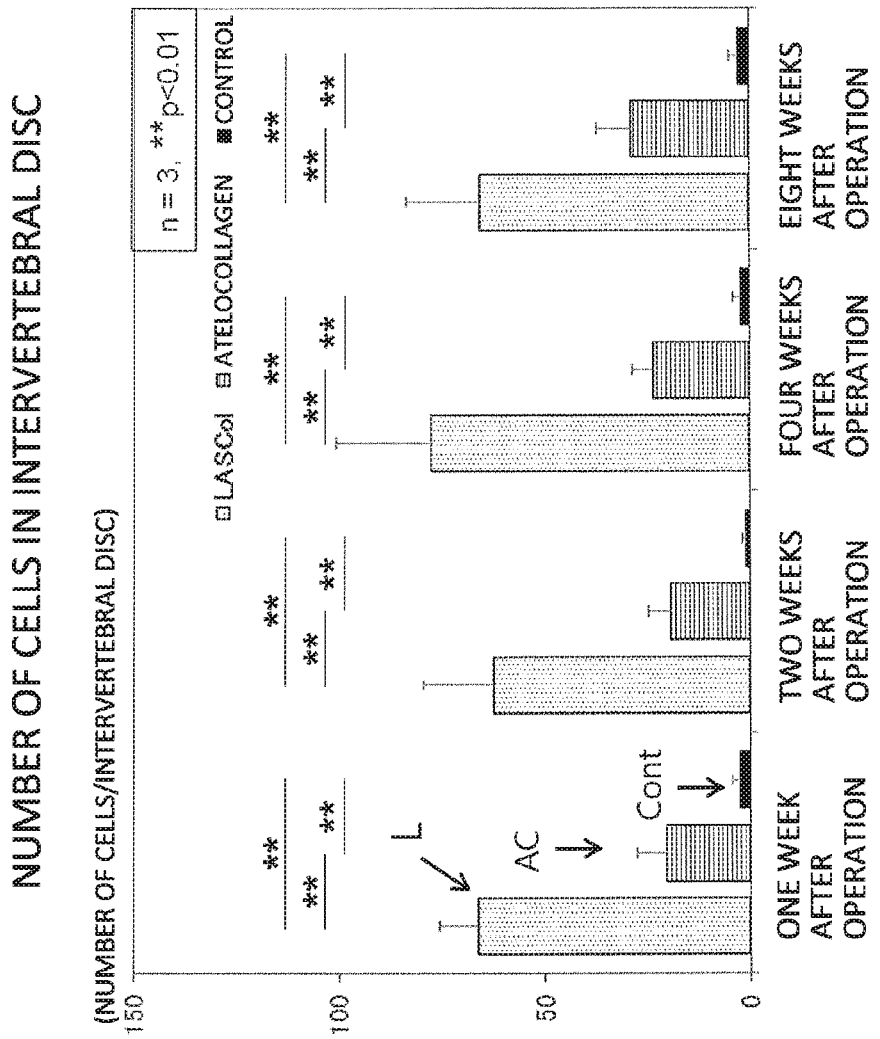
FIG. 19 is a graph showing the result of counting cells that have infiltrated into the nucleus pulposus region in FIGS. 14 to 17.

FIG. 19 shows the result of cell counting of cells that had infiltrated into the nucleus pulposus region in FIG. 14 to FIG. 17. The horizontal axis represents time in weeks after operation and the vertical axis represents the number of cells that have infiltrated into the nucleus pulposus region per intervertebral disc (number of cells/intervertebral disc). The results for the LASCol-receiving group, the AC-receiving group, and the control group at specified weeks after operation are shown side by side. In the part for one week after operation, the LASCol-receiving group was labeled as "L," the atelocollagen-receiving group was labeled as "AC," and the control group was labeled as "Cont."

The average numbers of cells one week after operation for the LASCol-receiving group, the atelocollagen-receiving group, and the control group were 66.3±9.4, 20.4±7.1, and 2.3±2.2, respectively. The average numbers of cells two weeks after operation were 62.4±17.4, 19.2±5.6, and 1.0±0.7, respectively. The average numbers of cells four weeks after operation were 77.8±23.2, 23.3±5.3, and 2.0±2.2, respectively. The average numbers of cells eight weeks after operation were 65.8±18.0, 28.8±8.7, and 2.6±2.4, respectively.

At all the time points, the LASCol-receiving group showed a significantly greater number of cells than the other two groups, and the atelocollagen-receiving group showed a significantly greater number of cells than the control group. Furthermore, no significant change was seen in any of the groups from one to eight weeks after operation.

Figure 20:
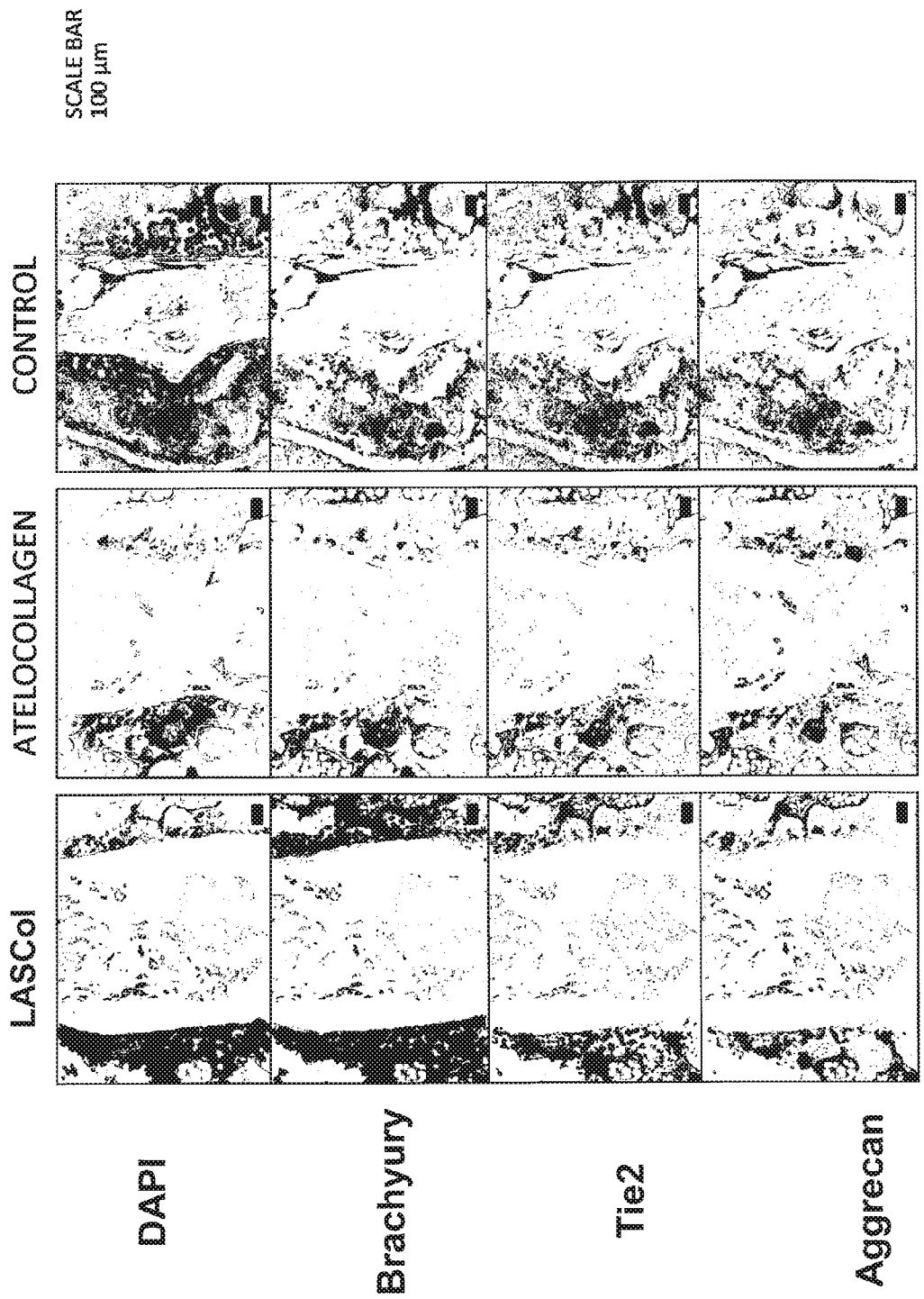
FIG. 20 is a black-and-white photograph that was converted from an image of multiple immunofluorescence staining of the nucleus pulposus region one week after operation.

FIG. 20 includes photographs obtained by image processing that converted the image of multiple immunofluorescence staining of the nucleus pulposus region one week after operation into a black-and-white one. The multiple immunofluorescence staining was performed by using DAPI, Brachyury, Tie2, and aggrecan. More specifically, an intervertebral disc of a rat tail and caudal vertebrae on either side of the intervertebral disc were removed, fixed with formalin, embedded in paraffin, and sectioned. Subsequently, the section was subjected to deparaffinization with xylene, antigen retrieval by a water bath heating method using buffer, and blocking with aqueous hydrogen peroxide. Then, the section was mounted after reacting each marker with a primary antibody and reacting the primary antibody with a labeled secondary antibody specific to the animal species of the primary antibody.

In the LASCol-receiving group, in the nucleus pulposus region, cells positive for Brachyury and Tie2 were observed, and strong staining of aggrecan was also observed. In contrast, in the atelocollagen-receiving group and in the control group, few cells positive for Brachyury and Tie2 were observed, and staining of aggrecan was also weak.

Figure 21:
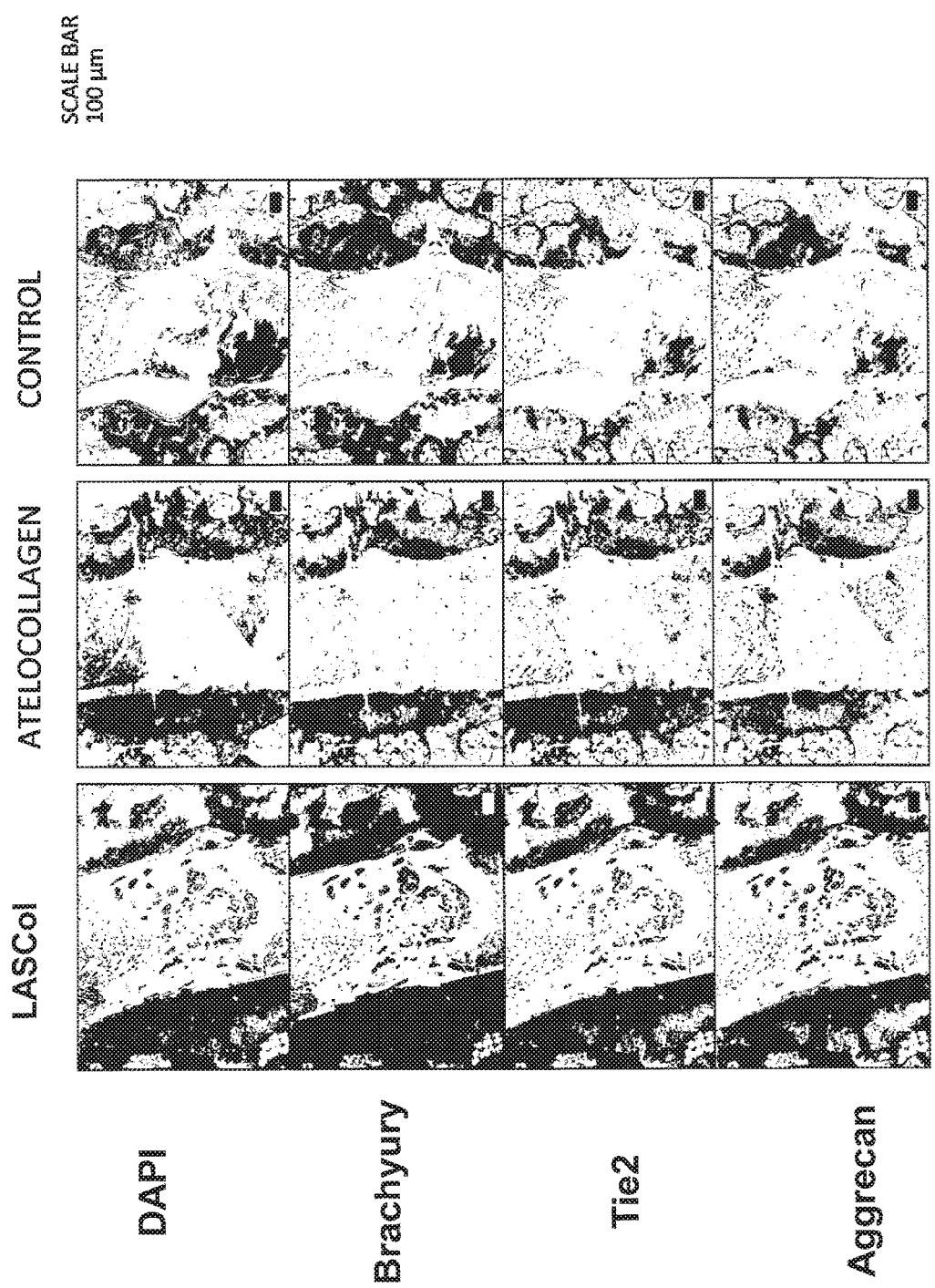
FIG. 21 includes photographs obtained by image processing that converted the image of multiple immunofluorescence staining of the nucleus pulposus region into a black-and-white one two weeks after operation.
Figure 22:
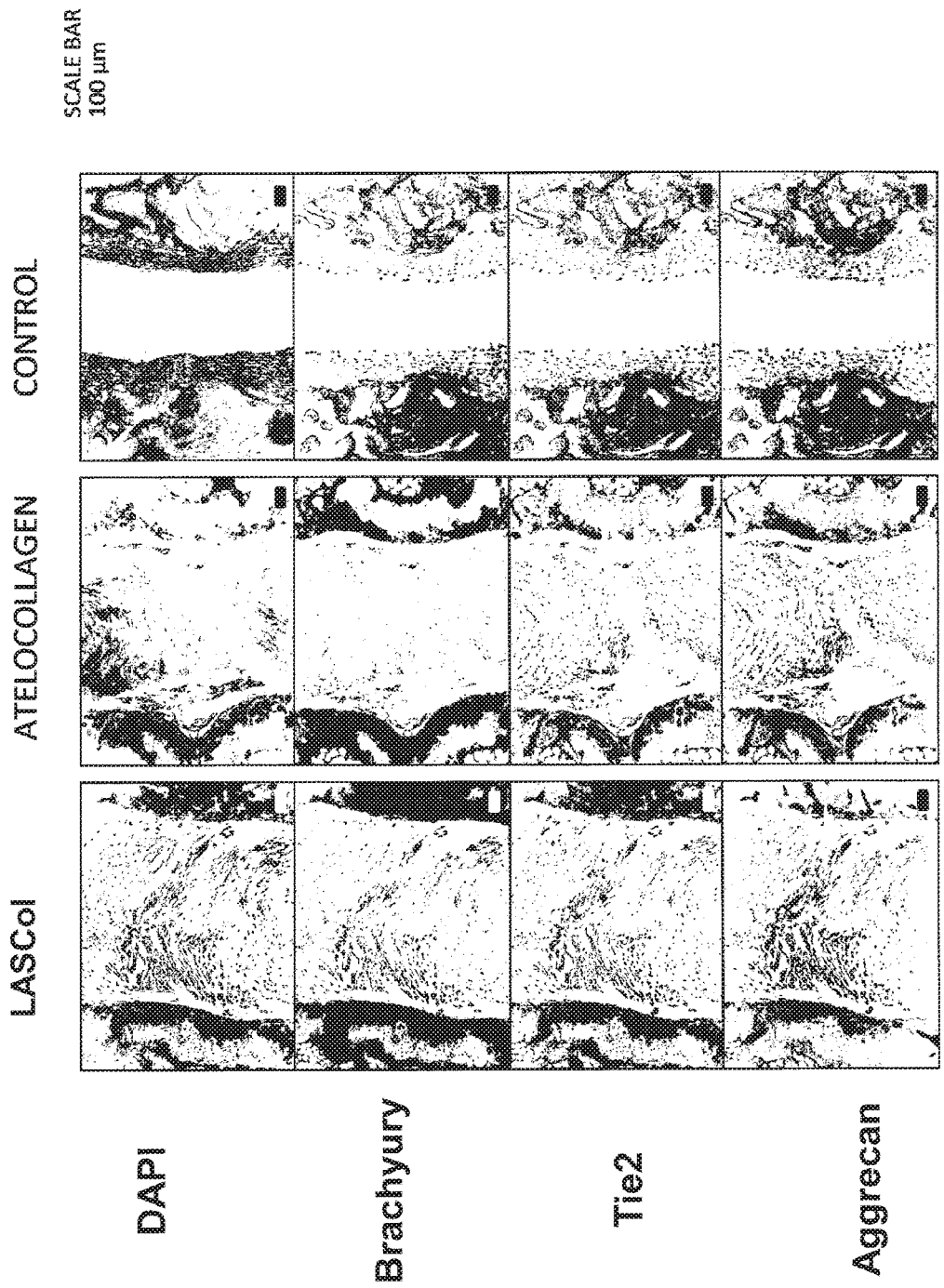
FIG. 22 includes photographs obtained by image processing that converted the image of multiple immunofluorescence staining of the nucleus pulposus region into a black-and-white one four weeks after operation.
Figure 23:
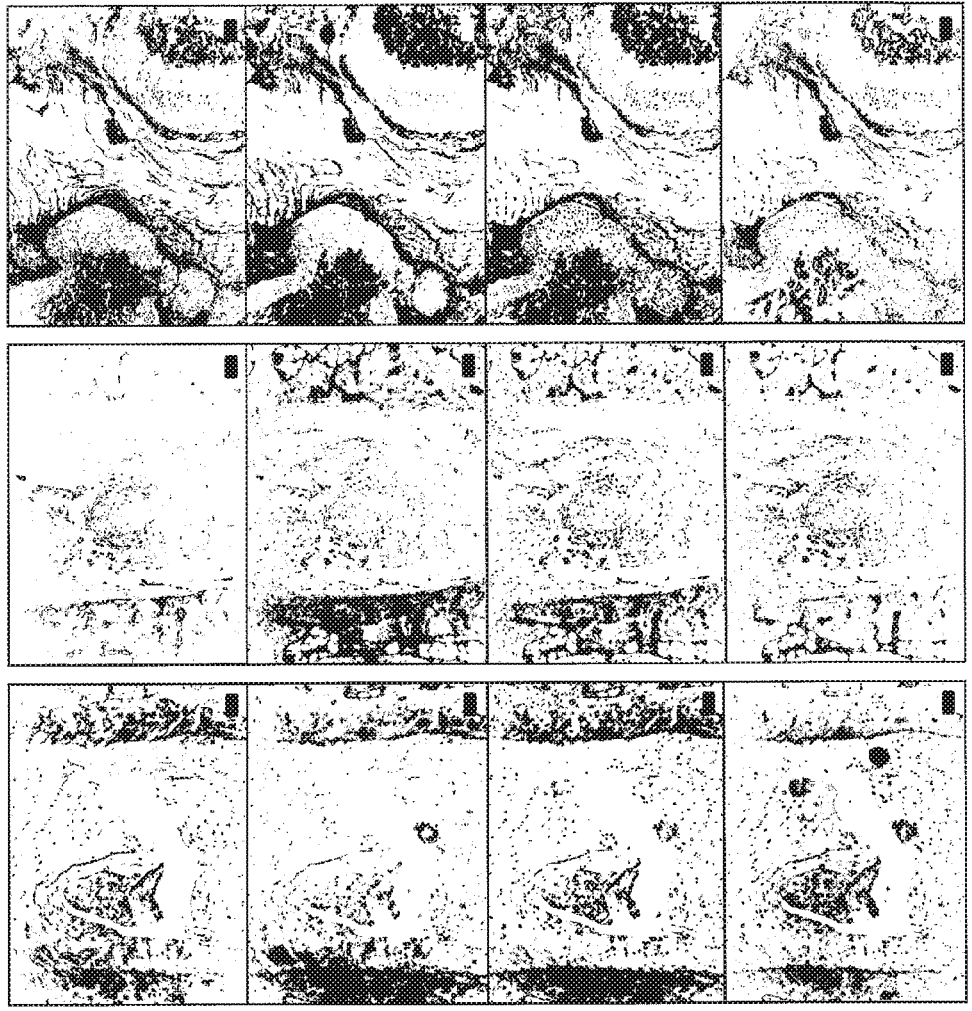
FIG. 23 includes photographs obtained by image processing that converted the image of multiple immunofluorescence staining of the nucleus pulposus region into a black-and-white one eight weeks after operation.

FIG. 21, FIG. 22, and FIG. 23 are photographs obtained by image processing that converted the image of multiple immunofluorescence staining of the nucleus pulposus region into a black-and-white one, wherein the staining was performed two weeks after operation, four weeks after operation, and eight weeks after operation, respectively. The results of multiple immunofluorescence staining had a similar tendency to FIG. 20.

Figure 24:
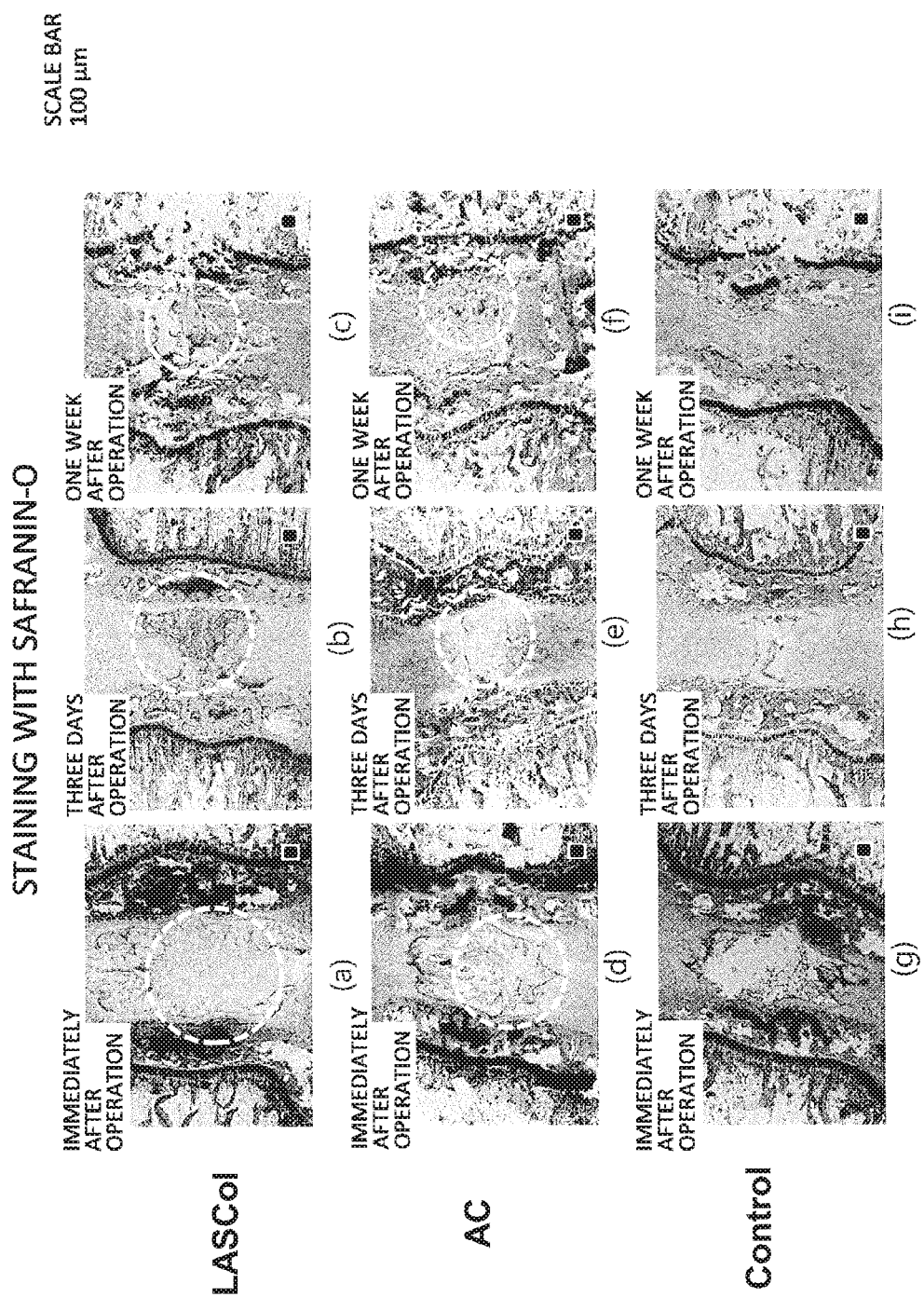
FIG. 24 includes photographs showing the tissue specimen of the nucleus pulposus region of the rat caudal vertebra that was stained with safranin O immediately after operation, three days after operation, and one week after operation.

FIG. 24 includes photographs showing the results of is safranin O staining of the nucleus pulposus region immediately after operation, three days after operation, and one week after operation. FIGS. 24(a) to 24(c) are the photographs of the LASCol-receiving group (indicated as "LASCol"), FIGS. 24(d) to 24(f) are the photographs of the atelocollagen-receiving group (indicated as "AC"), and FIGS. 24(g) to 24(i) are the photographs of the control group (indicated as "Control").

In the LASCol-receiving group, LASCol gel that was stained green was observed in the nucleus pulposus region immediately after operation. Infiltration of many cells was observed in the gel three days after operation and one week after operation. In the atelocollagen-receiving group, collagen gel that was stained green was also observed in the nucleus pulposus region from immediately after operation to one week after operation, but only a few cells were observed on the gel surface three days after operation and one week after operation. In the control group, the nucleus pulposus region was hollow immediately after operation and three days after operation; and the nucleus pulposus region was collapsed, and moreover, no cell infiltration was observed one week after operation. As described above, cell infiltration was observed three days after LASCol administration.

Figure 25:
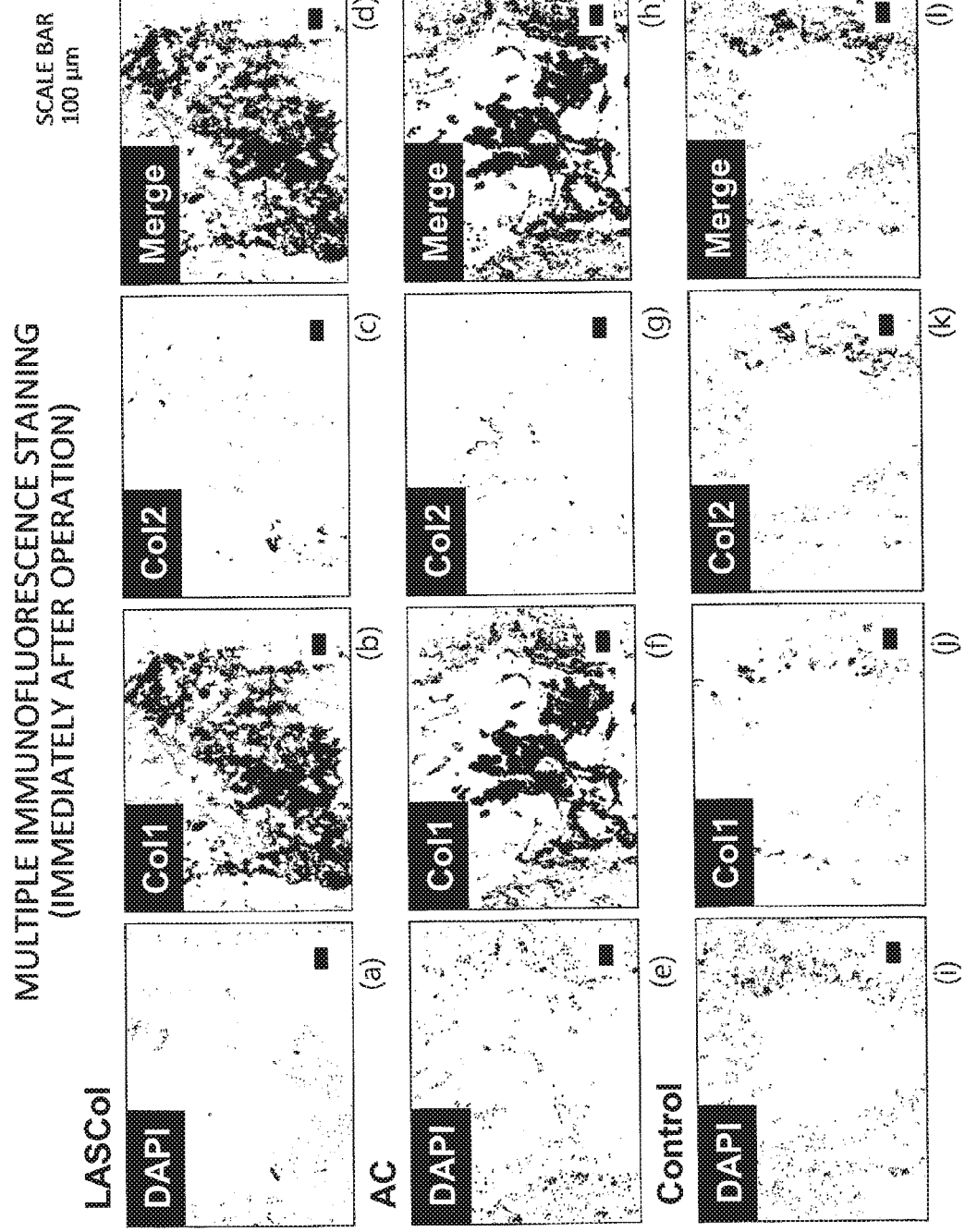
FIG. 25 includes photographs obtained by image processing that converted the image of multiple immunofluorescence staining of the nucleus pulposus region into a black-and-white one immediately after operation.
Figure 26:
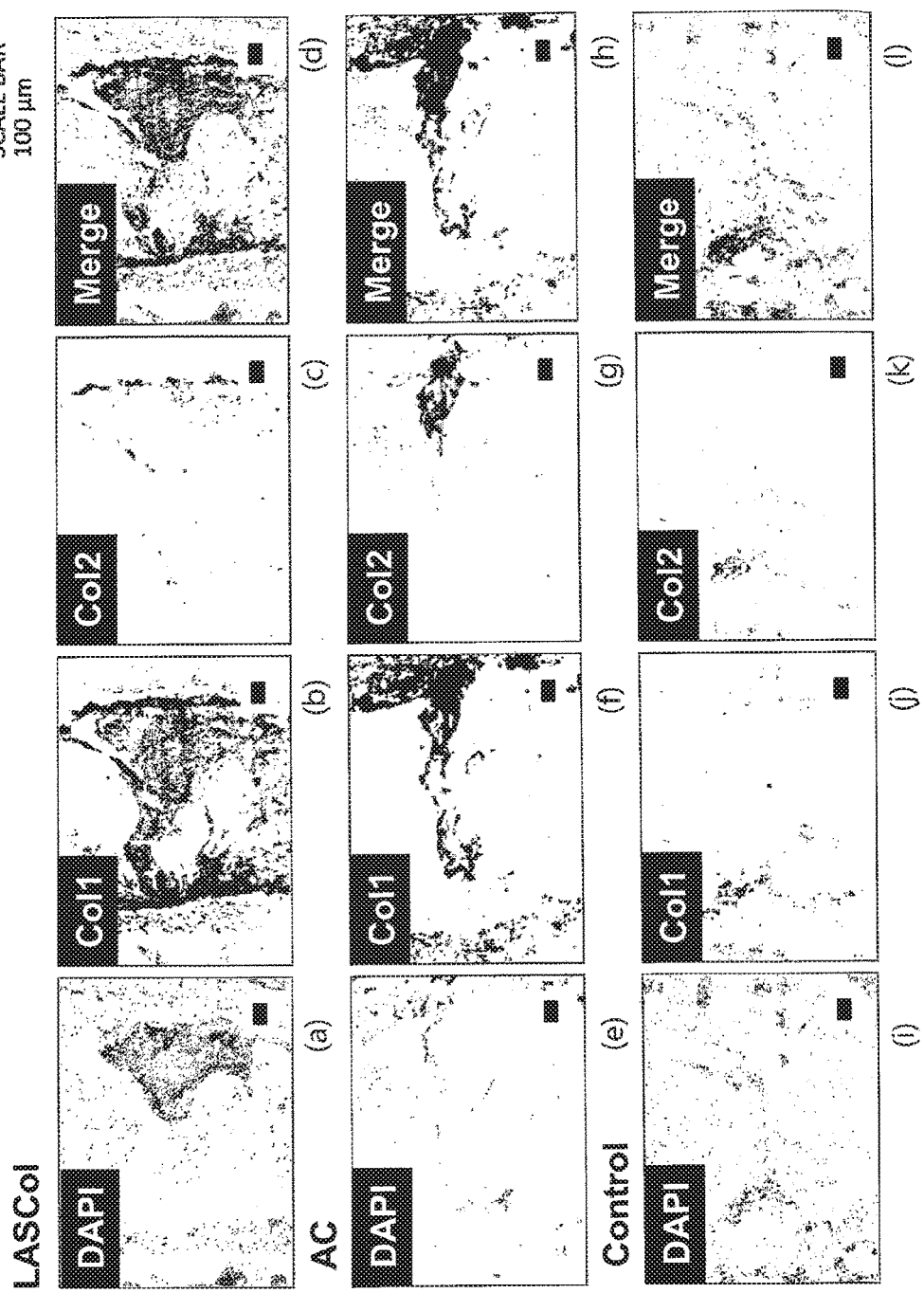
FIG. 26 includes photographs obtained by image processing that converted the image of multiple immunofluorescence staining of the nucleus pulposus region into a black-and-white one three days after operation.
Figure 27:
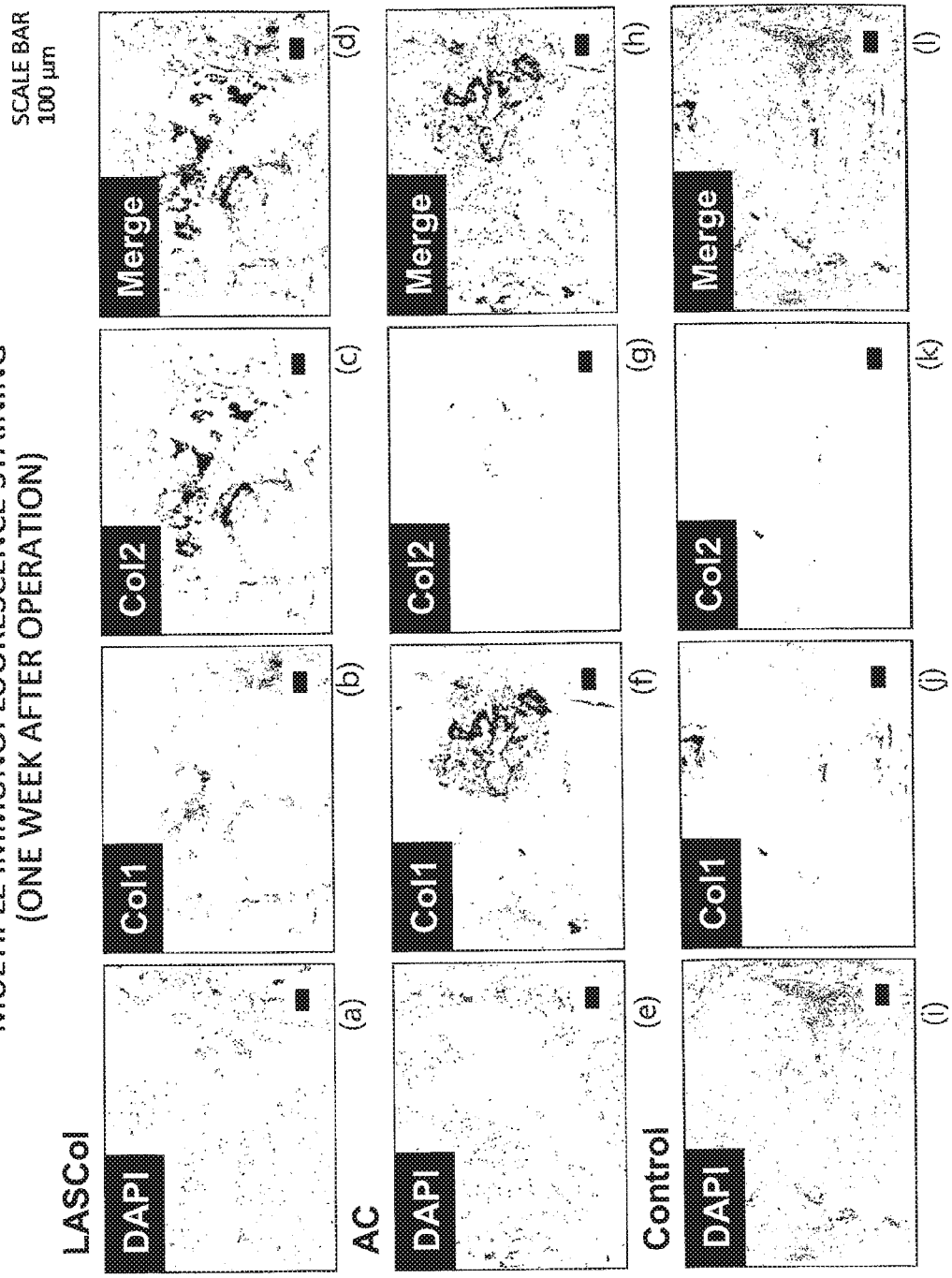
FIG. 27 includes photographs obtained by image processing that converted the image of multiple immunofluorescence staining of the nucleus pulposus region into a black-and-white one 1 week after operation.
Figure 28:
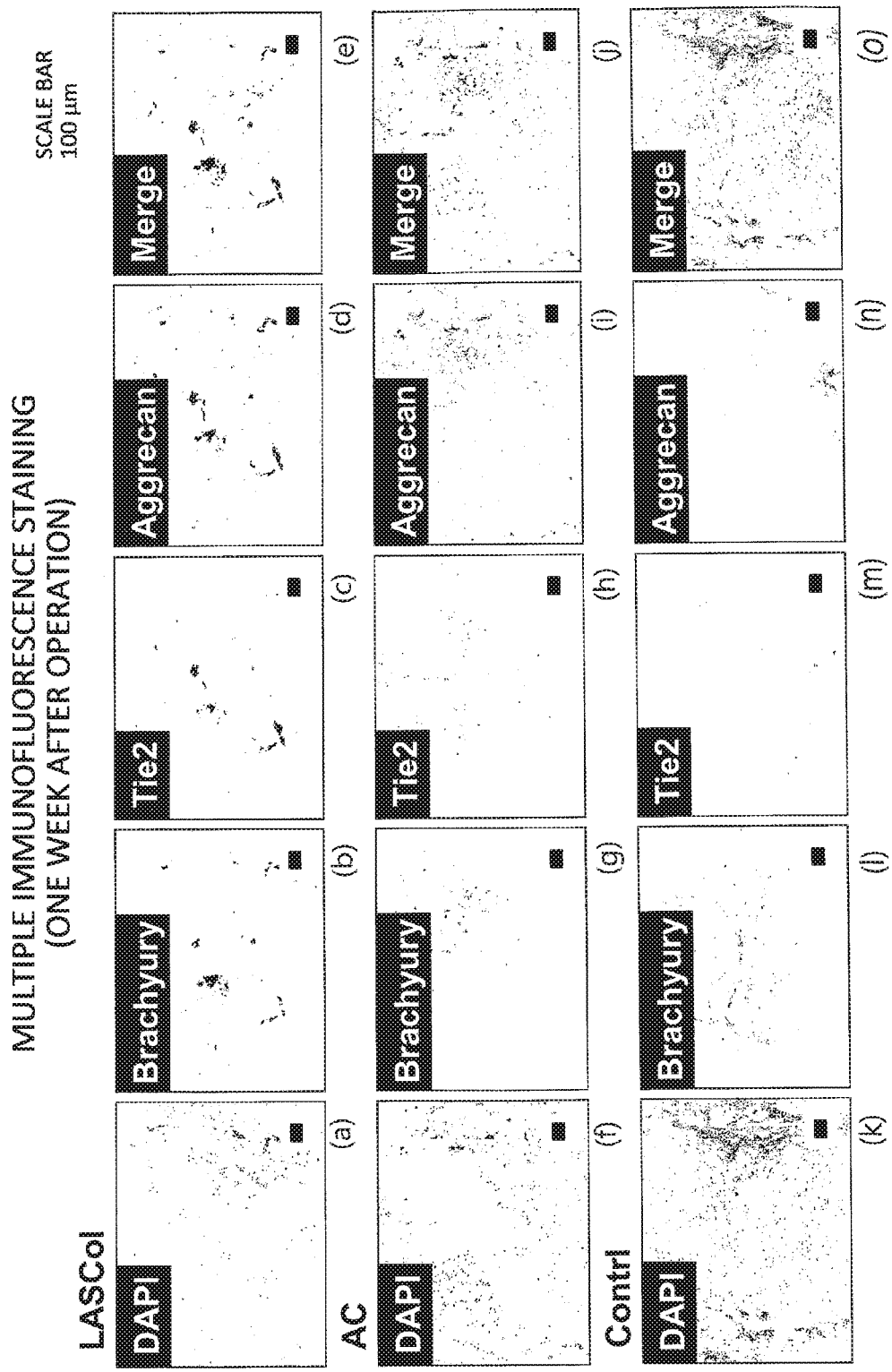
FIG. 28 includes photographs obtained by image processing that converted the image of multiple immunofluorescence staining of the nucleus pulposus region into a black-and-white one 1 week after operation.

FIGS. 25 to 30 show the photographs of multiple immunofluorescence staining of the nucleus pulposus region. FIG. 25 shows staining immediately after operation, FIG. 26 shows staining three days after operation, and FIGS. 27 to 29 show staining one week after operation. The LASCol-receiving group, the atelocollagen-receiving group, and the control group are indicated as "LASCol," "AC," and "Control," respectively.

Reference is made to FIG. 25 (immediately after operation.). FIGS. 25(a) to 25(d) represent the LASCol-receiving group, FIGS. 25(e) to 25(h) represent the atelocollagen-receiving groups, and FIGS. 25(i) to 25(l) represent the control group. The figures show the results of staining with DAPI, Col1 (reacts with collagen I), and Col2 (reacts with collagen II) for each group. "Merge" represents a merged photograph of FIG. 25.

In the LASCol-receiving group and the atelocollagen-receiving group, an area densely stained with Col1 was observed in the nucleus pulposus region, which indicated the presence of the respective injected collagen gels. Furthermore, both the LASCol-receiving group and the atelocollagen-receiving group were negative for Col2. Furthermore, hardly any part was stained in staining with DAPI in all three groups, which revealed that most nucleus pulposus cells were removed.

Reference is made to FIG. 26 (three days after operation). FIGS. 26(a) to 26(d) represent the LASCol-receiving group, FIGS. 26(e) to 26(h) represent the atelocollagen-receiving groups, and FIGS. 26(i) to 26(l) represent the control group. The figures show the results of staining with DAPI, Col1 (reacts with collagen I), and Col2 (reacts with collagen II) for each group. "Merge" represents a merged photograph of FIG. 26.

In the LASCol-receiving group, a Col1-positive area was observed in a part where DAPI showed aggregation of cells, which indicated that the cells had infiltrated into the LASCol gel. Hardly any Col2-positive part was observed within the nucleus pulposus region. In the atelocollagen group, Col1-positive atelocollagen was observed, but this stayed on the gel surface and no cell infiltration into the gel was observed.

Reference is made to FIG. 27 (one week after operation). FIGS. 27(a) to 27(d) represent the LASCol-receiving group, FIGS. 27(e) to 27(h) represent the atelocollagen-receiving groups, and FIGS. 27(i) to 27(l) represent the control group. The figures show the results of staining with DAPI, Col1 (reacts with collagen I), and Col2 (reacts with collagen II) for each group. "Merge" represents a merged photograph of FIG. 27.

In the LASCol-receiving group, a part showing aggregation of cells was positive for Col2. On the other hand, only week staining with Col1 was observed. In the atelocollagen-receiving group, Col1-positive atelocollagen gel was found to remain and no Col1-positive area was observed. In the control group, a Col1-positive part was observed partly in the annulus fibrosus cell region.

Reference is made to FIG. 28 (one week after operation). FIGS. 28(a) to 28(e) represent the LASCol-receiving group, FIGS. 28(f) to 28(j) represent the atelocollagen-receiving groups, and FIGS. 28(k) to 28(o) represent the control group. These figures show the result of staining by using DAPI, Brachyury, Tie2, and aggrecan for each group. "Merge" represents a merged photograph in FIG. 28.

In the LASCol-receiving group, DAPI showed aggregation of cells. Furthermore, although the quantity was small, cells positive for Brachyury and Tie2 were observed within the nucleus pulposus region. In the atelocollagen-receiving group, cells presumed to be remaining cells were observed but these cells were negative for both Brachyury and Tie2. In the control group, the nucleus pulposus region was collapsed because of compression by the annulus fibrosus region.

As described above, the therapeutic agent of the present invention that is used for treating intervertebral disc degeneration can regenerate nucleus pulposus when filled into the nucleus pulposus region from which nucleus pulposus cells had escaped. It has, by itself, the intervertebral space-maintaining ability at a concentration of 21 mg/ml or higher. Therefore, it is possible to regenerate the nucleus pulposus while maintaining a certain distance between vertebrae. Furthermore, since LASCol turns into gel when a concentration thereof is 3.5 mg/ml or higher, a similar therapeutic effect can be expected by using LASCol together with another auxiliary substance that has the intervertebral space-maintaining ability. The inventive therapeutic agent is highly safe because neither living cell nor nucleus pulposus cell from a donor is used therefor.

Furthermore, the material for culturing intervertebral disc cell (nucleus pulposus cell and/or annulus fibrosus cell) according to the present invention promotes spheroid by the nucleus pulposus cells and/or the annulus fibrosus cells and enables culturing spheroids, each of which includes many cells.

INDUSTRIAL APPLICABILITY

The therapeutic agent for intervertebral disc degeneration according to the present invention can be favorably used for treating intervertebral disc degeneration. The material for culturing intervertebral disc cells according to the present invention enables culturing a nucleus pulposus cell and/or an annulus fibrosus cell.

The invention claimed is:

1. A therapeutic agent for intervertebral disc degeneration, comprising:

Low Adhesive Scaffold Collagen (LASCol) at a concentration of 21 mg/ml or higher, and a growth factor, wherein the growth factor is a compound selected from the group consisting of Osteogenic Protein-1 (OP-1), bFGF, TGF-β1, GDF-5, BMP2, VEGF, and IGF-1;

wherein the LASCol is in a gel state, wherein the LASCol contains a degradation product of collagen or atelocollagen in which a chemical bond between $Y_1$ and $Y_2$ of an α1 chain is cleaved in an amino-terminal amino acid sequence including a triple helical domain of the collagen or atelocollagen, the sequence being shown by the following (A), or a chemical bond between G and $X_3$ of an α2 chain is cleaved in an amino-terminal amino acid sequence including a triple helical domain of the collagen or atelocollagen, the sequence being shown by the following (B), (SEQ ID NO: 1)
(A) $-Y_1-Y_2-Y_3-G-Y_4-Y_5-G-Y_6-Y_7-G-Y_8-Y_9-G-$ (where G represents glycine, and $Y_1$ to $Y_9$ each represents an amino acid), (SEQ ID NO: 2)
(B) $-G-X_1-X_2-G-X_3-X_4-G-X_5-X_6-G-$ (where G represents glycine, and $X_1$ to $X_6$ each represents an amino acid).

2. The therapeutic agent for intervertebral disc degeneration according to claim 1, further comprising at least one of hydrogel, gelatin gel, chitosan gel, hyaluronic acid-collagen hydrogel, a hyaluronic acid polymer, a hyaluronic acid-PEG polymer, collagen-hyaluronic acid-PEG hydrogel, and ultra-purified alginate gel.

3. A material for culturing intervertebral disc cells, comprising:

Low Adhesive Scaffold Collagen (LASCol) at a concentration of 21 mg/ml or higher, and a growth factor, wherein the growth factor is a compound selected from the group consisting of Osteogenic Protein-1 (OP-1), bFGF, TGF-β1, GDF-5, BMP2, VEGF, and IGF-1;

wherein the LASCol is in a gel state, wherein the LASCol contains a degradation product of collagen or atelocollagen in which a chemical bond between $Y_1$ and $Y_2$ of an α1 chain is cleaved in an amino-terminal amino acid sequence including a triple helical domain of the collagen or atelocollagen, the sequence being shown by the following (A), or a chemical bond between G and $X_3$ of an α2 chain is cleaved in an amino-terminal amino acid sequence including a triple helical domain of the collagen or atelocollagen, the sequence being shown by the following (B), (SEQ ID NO: 1)
(A) $-Y_1-Y_2-Y_3-G-Y_4-Y_5-G-Y_6-Y_7-G-Y_8-Y_9-G-$ (where G represents glycine, and $Y_1$ to $Y_9$ each represents an amino acid), (SEQ ID NO: 2)
(B) $-G-X_1-X_2-G-X_3-X_4-G-X_5-X_6-G-$ (where G represents glycine, and $X_1$ to $X_6$ each represents an amino acid).

4. The material for culturing intervertebral disc cells according to claim 3, further comprising at least one of hydrogel, gelatin gel, chitosan gel, hyaluronic acid-collagen hydrogel, a hyaluronic acid polymer, a hyaluronic acid-PEG polymer, collagen-hyaluronic acid-PEG hydrogel, and ultra-purified alginate gel.

5. A nucleus pulposus cell regenerated by injecting the therapeutic agent for intervertebral disc degeneration according to claim 1 into a nucleus pulposus region.

6. An annulus fibrosus cell regenerated by injecting the therapeutic agent for intervertebral disc degeneration according to claim 1 into a nucleus pulposus region.

* * * * *

SEQUENCE LISTING

```
<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: Partial Sequence of Protein
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
```

```
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 1

Xaa Xaa Xaa Gly Xaa Xaa Gly Xaa Xaa Gly Xaa Xaa Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Partial Sequence of Protein
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 2

Gly Xaa Xaa Gly Xaa Xaa Gly Xaa Xaa Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Partial Sequence of Protein

<400> SEQUENCE: 3

Val Pro Gly Pro Met Gly Pro Ser Gly Pro Arg Gly
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Partial Sequence of Protein

<400> SEQUENCE: 4

Met Gly Pro Ser Gly Pro Arg Gly
1               5

<210> SEQ ID NO 5
<211> LENGTH: 14
<212> TYPE: PRT
<213> ORGANISM: Artificial Sequence
<220> FEATURE:
<223> OTHER INFORMATION: Partial Sequence of Protein

<400> SEQUENCE: 5

Gly Pro Gly Pro Met Gly Leu Met Gly Pro Arg Gly Pro Pro
1               5                   10
```

```
<210> SEQ ID NO 6
<211> LENGTH: 8
<212> TYPE: PRT
<213> ORGANISM: Artificial Sequence
<220> FEATURE:
<223> OTHER INFORMATION: Partial Sequence of Protein

<400> SEQUENCE: 6

Leu Met Gly Pro Arg Gly Pro Pro
1               5
```